(12) United States Patent
Kiani et al.

(10) Patent No.: US 9,153,112 B1
(45) Date of Patent: Oct. 6, 2015

(54) MODULAR PATIENT MONITOR

(75) Inventors: Massi Joe E. Kiani, Laguna Niguel, CA (US); Ammar Al-Ali, San Juan Capistrano, CA (US); Michael O'Reilly, Dana Point, CA (US); Paul Ronald Jansen, San Clemente, CA (US); Nicholas Evan Barker, Laguna Beach, CA (US); Alejandro Garfio, West Covina, CA (US); Anand Sampath, Corona, CA (US)

(73) Assignee: MASIMO CORPORATION, Irvine, CA (US)

( * ) Notice: Subject to any disclaimer, the term of this patent is extended or adjusted under 35 U.S.C. 154(b) by 1044 days.

(21) Appl. No.: 13/039,218

(22) Filed: Mar. 2, 2011

Related U.S. Application Data

(63) Continuation of application No. 12/973,392, filed on Dec. 20, 2010, now abandoned.

(60) Provisional application No. 61/405,125, filed on Oct. 20, 2010, provisional application No. 61/288,843, (Continued)

(51) Int. Cl.
  *G08B 23/00*    (2006.01)
  *G08B 13/22*    (2006.01)

(52) U.S. Cl.
  CPC ..................................... *G08B 13/22* (2013.01)

(58) Field of Classification Search
  CPC ........ G08B 23/00; G08B 25/14; G08B 17/00; G08B 17/10; A61B 6/56; A61B 2560/0456
  USPC .......... 340/500, 573.1, 286.07; 600/485, 103, 600/110, 137, 215, 225, 193, 440
  See application file for complete search history.

(56) References Cited

U.S. PATENT DOCUMENTS

| 3,978,849 A | 9/1976 | Geneen |
| 4,108,166 A | 8/1978 | Schmid |

(Continued)

FOREIGN PATENT DOCUMENTS

| EP | 735499 A1 | 10/1996 |
| EP | 2 335 569 A2 | 6/2011 |

(Continued)

OTHER PUBLICATIONS

Extended European Search Report for European Application No. 10195398.2 dated Jul. 5, 2012.

(Continued)

*Primary Examiner* — Jennifer Mehmood
*Assistant Examiner* — Rufus Point
(74) *Attorney, Agent, or Firm* — Knobbe, Martens, Olson & Bear LLP

(57) ABSTRACT

A modular patient monitor provides a multipurpose, scalable solution for various patient monitoring applications. In an embodiment, a modular patient monitor utilizes multiple wavelength optical sensor and/or acoustic sensor technologies to provide blood constituent monitoring and acoustic respiration monitoring (ARM) at its core, including pulse oximetry parameters and additional blood parameter measurements such as carboxyhemoglobin (HbCO) and methemoglobin (HbMet). Expansion modules provide blood pressure BP, blood glucose, ECG, CO2, depth of sedation and cerebral oximetry to name a few.

Aspects of the present disclosure also include a transport dock for providing enhanced portability and functionally to handheld monitors. In an embodiment, the transport dock provides one or more docking interfaces for placing monitoring components in communication with other monitoring components. In an embodiment, the transport dock attaches to the modular patient monitor.

10 Claims, 44 Drawing Sheets

Related U.S. Application Data filed on Dec. 21, 2009, provisional application No. 61/290,436, filed on Dec. 28, 2009, provisional application No. 61/407,011, filed on Oct. 26, 2010, provisional application No. 61/407,033, filed on Oct. 27, 2010.

(56) References Cited

U.S. PATENT DOCUMENTS

| | | | |
|---|---|---|---|
| 4,231,354 A | 11/1980 | Kurtz et al. | |
| 4,589,415 A | 5/1986 | Haaga | |
| 4,662,378 A | 5/1987 | Thomis | |
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,092,340 A | 3/1992 | Yamaguchi et al. | |
| 5,140,519 A | 8/1992 | Friesdorf et al. | |
| 5,159,932 A | 11/1992 | Zanetti et al. | |
| 5,161,539 A | 11/1992 | Evans et al. | |
| 5,163,438 A | 11/1992 | Gordon et al. | |
| 5,262,944 A | 11/1993 | Weisner et al. | |
| 5,277,189 A | 1/1994 | Jacobs | |
| 5,278,627 A | 1/1994 | Aoyagi et al. | |
| 5,282,474 A | 2/1994 | Valdes Sosa et al. | |
| 5,318,037 A | 6/1994 | Evans et al. | |
| 5,319,355 A | 6/1994 | Russek | |
| 5,333,106 A | 7/1994 | Lanpher et al. | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,375,599 A | 12/1994 | Shimizu | |
| 5,377,676 A | 1/1995 | Vari et al. | |
| 5,400,794 A | 3/1995 | Gorman | |
| D359,546 S | 6/1995 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,483,968 A | 1/1996 | Adam et al. | |
| 5,490,505 A | 2/1996 | Diab et al. | |
| 5,494,041 A | 2/1996 | Wilk | |
| 5,494,043 A | 2/1996 | O'Sullivan et al. | |
| 5,503,149 A | 4/1996 | Beavin | |
| 5,505,202 A | 4/1996 | Mogi et al. | |
| 5,533,511 A | 7/1996 | Kaspari et al. | |
| 5,534,851 A | 7/1996 | Russek | |
| 5,561,275 A | 10/1996 | Savage et al. | |
| 5,562,002 A | 10/1996 | Lalin | |
| 5,579,001 A * | 11/1996 | Dempsey et al. | 340/870.01 |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,640,967 A | 6/1997 | Fine et al. | |
| 5,645,440 A | 7/1997 | Tobler et al. | |
| 5,685,299 A | 11/1997 | Diab et al. | |
| 5,685,314 A * | 11/1997 | Geheb et al. | 600/513 |
| 5,724,983 A | 3/1998 | Selker et al. | |
| 5,725,308 A | 3/1998 | Smith et al. | |
| 5,734,739 A | 3/1998 | Sheehan et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,822,546 A * | 10/1998 | George | 710/303 |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,910,139 A * | 6/1999 | Cochran et al. | 606/1 |
| 5,919,134 A | 7/1999 | Diab | |
| 5,921,920 A | 7/1999 | Marshall et al. | |
| 5,931,160 A | 8/1999 | Gilmore et al. | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,032,678 A | 3/2000 | Rottem | |
| 6,035,230 A | 3/2000 | Kang et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,106,463 A | 8/2000 | Wilk | |
| 6,110,522 A | 8/2000 | Lepper, Jr. et al. | |
| 6,124,597 A | 9/2000 | Shehada | |
| 6,128,521 A | 10/2000 | Marro et al. | |
| 6,129,675 A | 10/2000 | Jay | |
| 6,132,218 A | 10/2000 | Benja-Athon | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,183,417 B1 | 2/2001 | Geheb et al. | |
| 6,184,521 B1 | 2/2001 | Coffin, IV et al. | |
| 6,185,448 B1 | 2/2001 | Borovsky | |
| 6,195,576 B1 | 2/2001 | John | |
| 6,206,830 B1 | 3/2001 | Diab et al. | |
| 6,221,012 B1 * | 4/2001 | Maschke et al. | 600/301 |
| 6,224,553 B1 | 5/2001 | Nevo | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,253,097 B1 | 6/2001 | Aronow et al. | |
| 6,256,523 B1 | 7/2001 | Diab et al. | |
| 6,263,222 B1 | 7/2001 | Diab et al. | |
| 6,269,262 B1 | 7/2001 | Kandori et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,301,493 B1 | 10/2001 | Marro et al. | |
| 6,317,627 B1 | 11/2001 | Ennen et al. | |
| 6,321,100 B1 | 11/2001 | Parker | |
| 6,325,761 B1 | 12/2001 | Jay | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,385,476 B1 | 5/2002 | Osadchy et al. | |
| 6,388,240 B2 | 5/2002 | Schulz et al. | |
| 6,397,091 B2 | 5/2002 | Diab et al. | |
| 6,430,437 B1 | 8/2002 | Marro | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,487 B1 | 2/2003 | Parker | |
| 6,524,240 B1 | 2/2003 | Thede | |
| 6,525,386 B1 | 2/2003 | Mills et al. | |

(56) References Cited

U.S. PATENT DOCUMENTS

| | | |
|---|---|---|
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 * | 6/2003 | Ali et al. .................. 600/323 |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,641,533 B2 | 11/2003 | Causey et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Pishney et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,719,694 B2 | 4/2004 | Weng et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,751,492 B2 | 6/2004 | Ben-haim |
| 6,760,607 B2 | 7/2004 | Al-Ali |
| 6,770,028 B1 | 8/2004 | Ali et al. |
| 6,771,994 B2 | 8/2004 | Kiani et al. |
| 6,783,492 B2 | 8/2004 | Dominguez |
| 6,790,178 B1 | 9/2004 | Mault et al. |
| 6,792,300 B1 | 9/2004 | Diab et al. |
| 6,795,724 B2 | 9/2004 | Hogan |
| 6,807,050 B1 | 10/2004 | Whitehorn et al. |
| 6,813,511 B2 | 11/2004 | Diab et al. |
| 6,816,741 B2 | 11/2004 | Diab |
| 6,817,979 B2 | 11/2004 | Nihtila et al. |
| 6,822,564 B2 | 11/2004 | Al-Ali |
| 6,826,419 B2 | 11/2004 | Diab et al. |
| 6,830,711 B2 | 12/2004 | Mills et al. |
| 6,837,848 B2 | 1/2005 | Bonner et al. |
| 6,841,535 B2 | 1/2005 | Divita et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,855,112 B2 | 2/2005 | Kao et al. |
| 6,860,266 B2 | 3/2005 | Blike |
| 6,861,639 B2 | 3/2005 | Al-Ali |
| 6,898,452 B2 | 5/2005 | Al-Ali et al. |
| 6,915,149 B2 | 7/2005 | Ben-haim |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,980,419 B2 | 12/2005 | Smith et al. |
| 6,983,179 B2 | 1/2006 | Ben-haim |
| 6,985,764 B2 | 1/2006 | Mason et al. |
| 6,993,371 B2 | 1/2006 | Kiani et al. |
| 6,996,427 B2 | 2/2006 | Ali et al. |
| 6,997,884 B2 | 2/2006 | Ulmsten |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,025,729 B2 | 4/2006 | De Chazal et al. |
| 7,027,849 B2 | 4/2006 | Al-Ali |
| 7,030,749 B2 | 4/2006 | Al-Ali |
| 7,033,761 B2 | 4/2006 | Shafer |
| 7,035,686 B2 | 4/2006 | Hogan |
| 7,039,449 B2 | 5/2006 | Al-Ali |
| 7,041,060 B2 | 5/2006 | Flaherty et al. |
| 7,044,918 B2 | 5/2006 | Diab |
| 7,063,666 B2 | 6/2006 | Weng et al. |
| 7,067,893 B2 | 6/2006 | Mills et al. |
| 7,079,035 B2 | 7/2006 | Bock et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,188,621 B2 | 3/2007 | DeVries et al. |
| 7,190,261 B2 | 3/2007 | Al-Ali |
| 7,208,119 B1 | 4/2007 | Kurtock et al. |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,229,415 B2 | 6/2007 | Schwartz |
| 7,239,905 B2 | 7/2007 | Kiani-Azarbayjany et al. |
| 7,241,287 B2 | 7/2007 | Shehada et al. |
| 7,244,251 B2 | 7/2007 | Shehada et al. |
| 7,245,953 B1 | 7/2007 | Parker |
| 7,252,659 B2 | 8/2007 | Shehada et al. |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,264,616 B2 | 9/2007 | Shehada et al. |
| 7,267,671 B2 | 9/2007 | Shehada et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,285,090 B2 | 10/2007 | Stivoric |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,313,423 B2 | 12/2007 | Griffin et al. |
| 7,314,446 B2 | 1/2008 | Byrd et al. |
| 7,322,971 B2 | 1/2008 | Shehada et al. |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,178 B2 | 4/2008 | Ziel et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,413,546 B2 | 8/2008 | Agutter et al. |
| 7,415,297 B2 | 8/2008 | Al-Ali et al. |
| 7,419,483 B2 | 9/2008 | Shehada |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,462,151 B2 | 12/2008 | Childre et al. |

(56) References Cited

U.S. PATENT DOCUMENTS

| | | |
|---|---|---|
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,250 B2 | 2/2009 | Bock et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,497,828 B1 | 3/2009 | Wilk et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,549,961 B1 * | 6/2009 | Hwang .................. 600/440 |
| 7,551,717 B2 | 6/2009 | Tome et al. |
| 7,559,520 B2 * | 7/2009 | Quijano et al. .......... 248/309.1 |
| 7,563,110 B2 | 7/2009 | Al-Ali et al. |
| 7,577,475 B2 | 8/2009 | Cosentino et al. |
| 7,596,398 B2 | 9/2009 | Al-Ali et al. |
| 7,597,665 B2 | 10/2009 | Wilk et al. |
| 7,612,999 B2 | 11/2009 | Clark et al. |
| 7,618,375 B2 | 11/2009 | Flaherty |
| D606,659 S | 12/2009 | Kiani et al. |
| 7,639,145 B2 | 12/2009 | Lawson et al. |
| 7,647,083 B2 | 1/2010 | Al-Ali et al. |
| D609,193 S | 2/2010 | Al-Ali et al. |
| 7,654,966 B2 | 2/2010 | Westinskow et al. |
| 7,684,845 B2 | 3/2010 | Juan |
| 7,689,437 B1 | 3/2010 | Teller et al. |
| RE41,236 E | 4/2010 | Seely |
| D614,305 S | 4/2010 | Al-Ali et al. |
| 7,693,697 B2 | 4/2010 | Westenskow et al. |
| RE41,317 E | 5/2010 | Parker |
| 7,729,733 B2 | 6/2010 | Al-Ali et al. |
| 7,734,320 B2 | 6/2010 | Al-Ali |
| 7,736,318 B2 | 6/2010 | Cosentino et al. |
| 7,761,127 B2 | 7/2010 | Al-Ali et al. |
| 7,761,128 B2 | 7/2010 | Al-Ali et al. |
| 7,763,420 B2 | 7/2010 | Strizker et al. |
| 7,764,982 B2 | 7/2010 | Dalke et al. |
| D621,516 S | 8/2010 | Kiani et al. |
| 7,766,818 B2 | 8/2010 | Iketani et al. |
| 7,774,060 B2 | 8/2010 | Westenskow et al. |
| 7,778,851 B2 | 8/2010 | Schoenberg et al. |
| 7,791,155 B2 | 9/2010 | Diab |
| 7,794,407 B2 | 9/2010 | Rothenberg |
| 7,801,581 B2 | 9/2010 | Diab |
| 7,820,184 B2 | 10/2010 | Strizker et al. |
| 7,822,452 B2 | 10/2010 | Schurman et al. |
| RE41,912 E | 11/2010 | Parker |
| 7,841,986 B2 | 11/2010 | He et al. |
| 7,844,313 B2 | 11/2010 | Kiani et al. |
| 7,844,314 B2 | 11/2010 | Al-Ali |
| 7,844,315 B2 | 11/2010 | Al-Ali |
| 7,858,322 B2 | 12/2010 | Tymianski et al. |
| 7,865,222 B2 | 1/2011 | Weber et al. |
| 7,865,232 B1 | 1/2011 | Krishnaswamy et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,890,156 B2 | 2/2011 | Ooi et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,914,514 B2 | 3/2011 | Calderon |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,963,927 B2 | 6/2011 | Kelleher et al. |
| 7,967,749 B2 | 6/2011 | Hutchinson et al. |
| 7,976,472 B2 | 7/2011 | Kiani |
| 7,988,637 B2 | 8/2011 | Diab |
| 7,988,639 B2 | 8/2011 | Starks |
| 7,990,382 B2 | 8/2011 | Kiani |
| 7,991,446 B2 | 8/2011 | Ali et al. |
| 7,991,463 B2 | 8/2011 | Kelleher et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,033,996 B2 | 10/2011 | Behar |
| 8,036,727 B2 | 10/2011 | Schurman et al. |
| 8,036,728 B2 | 10/2011 | Diab et al. |
| 8,036,736 B2 | 10/2011 | Snyder et al. |
| 8,038,625 B2 | 10/2011 | Afonso et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,068,104 B2 | 11/2011 | Rampersad |
| 8,073,707 B2 | 12/2011 | Teller et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,206,312 B2 | 6/2012 | Farquhar |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,235,907 B2 | 8/2012 | Wilk et al. |
| 8,239,780 B2 | 8/2012 | Manetta et al. |
| 8,241,213 B2 | 8/2012 | Lynn et al. |
| 8,244,325 B2 | 8/2012 | Al-Ali et al. |
| 8,249,815 B2 | 8/2012 | Taylor |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,294,716 B2 | 10/2012 | Lord et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,311,747 B2 | 11/2012 | Taylor |
| 8,311,748 B2 | 11/2012 | Taylor et al. |
| 8,315,683 B2 | 11/2012 | Al-Ali et al. |
| 8,315,812 B2 | 11/2012 | Taylor |

(56) References Cited

U.S. PATENT DOCUMENTS

| | | |
|---|---|---|
| 8,315,813 B2 | 11/2012 | Taylor et al. |
| 8,315,814 B2 | 11/2012 | Taylor et al. |
| 8,321,150 B2 | 11/2012 | Taylor |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,360,936 B2 | 1/2013 | Dibenedetto et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,579,813 B2 | 11/2013 | Causey |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 2002/0052311 A1 | 5/2002 | Solomon et al. |
| 2002/0063690 A1* | 5/2002 | Chung et al. ............... 345/168 |
| 2002/0140675 A1* | 10/2002 | Ali et al. ..................... 345/158 |
| 2003/0027326 A1 | 2/2003 | Ulmsten et al. |
| 2004/0013647 A1 | 1/2004 | Solomon et al. |
| 2004/0073095 A1 | 4/2004 | Causey et al. |
| 2004/0090742 A1* | 5/2004 | Son et al. ..................... 361/686 |
| 2004/0122787 A1 | 6/2004 | Avinash et al. |
| 2004/0147818 A1 | 7/2004 | Levy et al. |
| 2004/0152957 A1 | 8/2004 | Stivoric et al. |
| 2004/0179332 A1 | 9/2004 | Smith et al. |
| 2004/0186357 A1 | 9/2004 | Soderberg et al. |
| 2004/0243017 A1 | 12/2004 | Causevic |
| 2004/0254432 A1 | 12/2004 | Shehada et al. |
| 2005/0020918 A1 | 1/2005 | Wilk et al. |
| 2005/0038332 A1 | 2/2005 | Saidara et al. |
| 2005/0038680 A1 | 2/2005 | McMahon |
| 2005/0065417 A1 | 3/2005 | Ali et al. |
| 2005/0080336 A1 | 4/2005 | Byrd et al. |
| 2005/0096542 A1 | 5/2005 | Weng et al. |
| 2005/0113653 A1 | 5/2005 | Fox et al. |
| 2005/0164933 A1 | 7/2005 | Tymianski et al. |
| 2005/0191294 A1 | 9/2005 | Arap et al. |
| 2005/0277872 A1* | 12/2005 | Colby et al. ..................... 604/67 |
| 2006/0058647 A1 | 3/2006 | Strommer et al. |
| 2006/0089543 A1 | 4/2006 | Kim et al. |
| 2006/0094936 A1 | 5/2006 | Russ |
| 2006/0149393 A1 | 7/2006 | Calderon |
| 2006/0155175 A1 | 7/2006 | Ogino et al. |
| 2006/0200009 A1 | 9/2006 | Wekell et al. |
| 2006/0217684 A1 | 9/2006 | Shehada et al. |
| 2006/0217685 A1 | 9/2006 | Shehada et al. |
| 2006/0224413 A1 | 10/2006 | Kim et al. |

(56) References Cited

U.S. PATENT DOCUMENTS

| | | |
|---|---|---|
| 2006/0235300 A1 | 10/2006 | Weng et al. |
| 2006/0253042 A1 | 11/2006 | Stahmann et al. |
| 2007/0000490 A1 | 1/2007 | DeVries et al. |
| 2007/0021675 A1 | 1/2007 | Childre et al. |
| 2007/0027368 A1 | 2/2007 | Collins et al. |
| 2007/0032733 A1 | 2/2007 | Burton |
| 2007/0055116 A1 | 3/2007 | Clark et al. |
| 2007/0055544 A1 | 3/2007 | Jung et al. |
| 2007/0060798 A1 | 3/2007 | Krupnik et al. |
| 2007/0088406 A1 * | 4/2007 | Bennett et al. .................. 607/60 |
| 2007/0118399 A1 | 5/2007 | Avinash et al. |
| 2007/0140475 A1 | 6/2007 | Kurtock et al. |
| 2007/0156033 A1 | 7/2007 | Causey et al. |
| 2007/0163589 A1 | 7/2007 | DeVries et al. |
| 2007/0232941 A1 | 10/2007 | Rabinovich |
| 2007/0244724 A1 | 10/2007 | Pendergast et al. |
| 2007/0255114 A1 | 11/2007 | Ackermann et al. |
| 2007/0255116 A1 | 11/2007 | Mehta et al. |
| 2007/0255250 A1 | 11/2007 | Moberg |
| 2008/0000479 A1 | 1/2008 | Elaz et al. |
| 2008/0003200 A1 | 1/2008 | Arap et al. |
| 2008/0021854 A1 | 1/2008 | Jung et al. |
| 2008/0033661 A1 | 2/2008 | Syroid et al. |
| 2008/0053438 A1 | 3/2008 | DeVries et al. |
| 2008/0058657 A1 | 3/2008 | Schwartz et al. |
| 2008/0090626 A1 | 4/2008 | Griffin et al. |
| 2008/0091089 A1 | 4/2008 | Guillory et al. |
| 2008/0091090 A1 | 4/2008 | Guillory et al. |
| 2008/0091471 A1 | 4/2008 | Michon et al. |
| 2008/0097167 A1 | 4/2008 | Yudkovitch et al. |
| 2008/0099366 A1 | 5/2008 | Niemiec et al. |
| 2008/0108884 A1 * | 5/2008 | Kiani .......................... 600/301 |
| 2008/0119412 A1 | 5/2008 | Tymianski et al. |
| 2008/0138278 A1 | 6/2008 | Scherz et al. |
| 2008/0171919 A1 | 7/2008 | Stivoric et al. |
| 2008/0208912 A1 | 8/2008 | Garibaldi |
| 2008/0221396 A1 | 9/2008 | Garces et al. |
| 2008/0228077 A1 | 9/2008 | Wilk et al. |
| 2008/0275309 A1 | 11/2008 | Stivoric et al. |
| 2008/0281167 A1 | 11/2008 | Soderberg et al. |
| 2008/0281168 A1 | 11/2008 | Gibson et al. |
| 2008/0281181 A1 | 11/2008 | Manzione et al. |
| 2008/0287751 A1 | 11/2008 | Stivoric et al. |
| 2008/0292172 A1 | 11/2008 | Assmann et al. |
| 2008/0319275 A1 | 12/2008 | Chiu et al. |
| 2008/0319354 A1 | 12/2008 | Bell et al. |
| 2009/0005651 A1 | 1/2009 | Ward et al. |
| 2009/0018808 A1 | 1/2009 | Bronstein et al. |
| 2009/0024008 A1 | 1/2009 | Brunner et al. |
| 2009/0052623 A1 | 2/2009 | Tome et al. |
| 2009/0054735 A1 | 2/2009 | Higgins et al. |
| 2009/0054743 A1 | 2/2009 | Stewart |
| 2009/0062682 A1 | 3/2009 | Bland et al. |
| 2009/0069642 A1 | 3/2009 | Gao et al. |
| 2009/0124867 A1 | 5/2009 | Hirsh et al. |
| 2009/0131759 A1 | 5/2009 | Sims et al. |
| 2009/0143832 A1 | 6/2009 | Saba |
| 2009/0157058 A1 | 6/2009 | Ferren et al. |
| 2009/0171225 A1 | 7/2009 | Gadodia et al. |
| 2009/0177090 A1 | 7/2009 | Grunwald et al. |
| 2009/0182287 A1 | 7/2009 | Kassab |
| 2009/0226372 A1 | 9/2009 | Ruoslahti et al. |
| 2009/0264778 A1 | 10/2009 | Markowitz et al. |
| 2009/0275844 A1 | 11/2009 | Al-Ali |
| 2009/0281462 A1 | 11/2009 | Heliot et al. |
| 2009/0299157 A1 | 12/2009 | Telfort et al. |
| 2010/0004518 A1 | 1/2010 | Vo et al. |
| 2010/0030040 A1 | 2/2010 | Poeze et al. |
| 2010/0030094 A1 | 2/2010 | Lundback |
| 2010/0036209 A1 | 2/2010 | Ferren et al. |
| 2010/0069725 A1 | 3/2010 | Al-Ali |
| 2010/0125217 A1 | 5/2010 | Kuo et al. |
| 2010/0144627 A1 | 6/2010 | Vitek et al. |
| 2010/0185101 A1 | 7/2010 | Sakai et al. |
| 2010/0198622 A1 | 8/2010 | Gajic et al. |
| 2010/0210958 A1 | 8/2010 | Manwaring et al. |
| 2010/0261979 A1 | 10/2010 | Kiani |
| 2010/0298659 A1 | 11/2010 | Mccombie et al. |
| 2010/0298661 A1 | 11/2010 | Mccombie et al. |
| 2010/0305412 A1 | 12/2010 | Darrah et al. |
| 2010/0312103 A1 | 12/2010 | Gorek et al. |
| 2010/0317936 A1 | 12/2010 | Al-Ali et al. |
| 2010/0317951 A1 | 12/2010 | Rutkowski et al. |
| 2011/0001605 A1 | 1/2011 | Kiani et al. |
| 2011/0021930 A1 | 1/2011 | Mazzeo et al. |
| 2011/0028809 A1 | 2/2011 | Goodman |
| 2011/0046495 A1 | 2/2011 | Osypka |
| 2011/0080294 A1 | 4/2011 | Tanishima et al. |
| 2011/0082711 A1 | 4/2011 | Poeze et al. |
| 2011/0087084 A1 | 4/2011 | Jeong et al. |
| 2011/0087117 A1 | 4/2011 | Tremper et al. |
| 2011/0087756 A1 | 4/2011 | Biondi |
| 2011/0098583 A1 | 4/2011 | Pandia et al. |
| 2011/0105854 A1 | 5/2011 | Kiani et al. |
| 2011/0118573 A1 | 5/2011 | Mckenna |
| 2011/0172967 A1 | 7/2011 | Al-Ali et al. |
| 2011/0184252 A1 | 7/2011 | Archer et al. |
| 2011/0184253 A1 | 7/2011 | Archer et al. |
| 2011/0208015 A1 | 8/2011 | Welch et al. |
| 2011/0208018 A1 | 8/2011 | Kiani |
| 2011/0208073 A1 | 8/2011 | Matsukawa et al. |
| 2011/0209915 A1 | 9/2011 | Telfort et al. |
| 2011/0212090 A1 | 9/2011 | Pedersen et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2011/0257544 A1 | 10/2011 | Kaasinen et al. |
| 2011/0295094 A1 | 12/2011 | Doyle et al. |
| 2012/0004579 A1 | 1/2012 | Luo et al. |
| 2012/0059230 A1 | 3/2012 | Teller et al. |
| 2012/0059267 A1 | 3/2012 | Lamego et al. |
| 2012/0071771 A1 | 3/2012 | Behar |
| 2012/0101353 A1 | 4/2012 | Reggiardo et al. |
| 2012/0116175 A1 | 5/2012 | Al-Ali et al. |
| 2012/0123799 A1 | 5/2012 | Nolen et al. |
| 2012/0136221 A1 | 5/2012 | Killen et al. |
| 2012/0179006 A1 | 7/2012 | Jansen et al. |
| 2012/0197619 A1 | 8/2012 | Namer Yelin et al. |
| 2012/0209082 A1 | 8/2012 | Al-Ali |
| 2012/0209084 A1 | 8/2012 | Olsen et al. |
| 2012/0226160 A1 | 9/2012 | Kudoh |
| 2012/0227739 A1 | 9/2012 | Kiani |
| 2012/0239434 A1 | 9/2012 | Breslow et al. |
| 2012/0265039 A1 | 10/2012 | Kiani |
| 2012/0282583 A1 | 11/2012 | Thaler et al. |
| 2012/0283524 A1 | 11/2012 | Kiani et al. |
| 2012/0286955 A1 | 11/2012 | Welch et al. |
| 2012/0294801 A1 | 11/2012 | Scherz et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0006131 A1 | 1/2013 | Narayan et al. |
| 2013/0006151 A1 | 1/2013 | Main et al. |
| 2013/0023775 A1 | 1/2013 | Lamego et al. |
| 2013/0035603 A1 | 2/2013 | Jarausch et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0079610 A1 | 3/2013 | Al-Ali |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0178749 A1 | 7/2013 | Lamego |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0262730 A1 | 10/2013 | Al-Ali et al. |
| 2013/0274571 A1 | 10/2013 | Diab et al. |
| 2013/0296672 A1 | 11/2013 | O'Neil et al. |

(56) References Cited

U.S. PATENT DOCUMENTS

| | | |
|---|---|---|
| 2013/0317327 A1 | 11/2013 | Al-Ali et al. |
| 2013/0317370 A1 | 11/2013 | Dalvi et al. |
| 2014/0336481 A1 | 11/2013 | Shakespeare et al. |
| 2013/0324808 A1 | 12/2013 | Al-Ali et al. |
| 2013/0324817 A1 | 12/2013 | Diab |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081097 A1 | 3/2014 | Al-Ali et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142399 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0343436 A1 | 11/2014 | Kiani |
| 2014/0357966 A1 | 12/2014 | Al-Ali et al. |

FOREIGN PATENT DOCUMENTS

| | | |
|---|---|---|
| EP | 2 766 834 | 8/2014 |
| JP | 2014/533997 | 12/2014 |
| WO | WO 2004/056266 | 7/2004 |
| WO | WO 2004/059551 | 7/2004 |
| WO | WO 2013/056160 | 4/2013 |

OTHER PUBLICATIONS

PCT International Search Report & Written Opinion for App. No. PCT/US2012/060109 dated Jun. 5, 2013, in 17 pages.

Wachter, S. Blake; Journal of the American Medical Informatics Association; The Employment of an Iterative Design Process to Develop a Pulmonary Graphical Display; vol. 10, No. 4, Jul./Aug. 2003; pp. 363-372.

PCT International Preliminary Report on Patentability for Application No. PCT/US2012/060109, dated Apr. 24, 2014.

PCT International Search Report & Written Opinion, App. No. PCT/US2014/060177, dated Dec. 19, 2014.

US 8,845,543, 09/2014, Diab et al. (withdrawn)

* cited by examiner

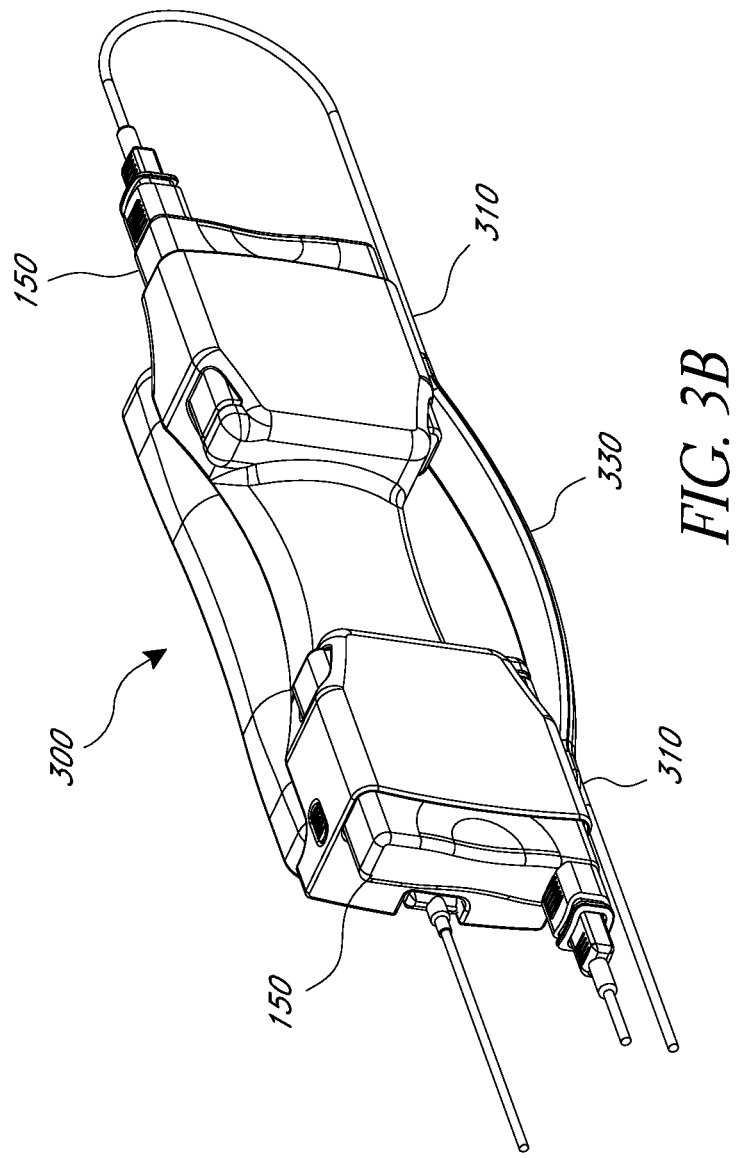

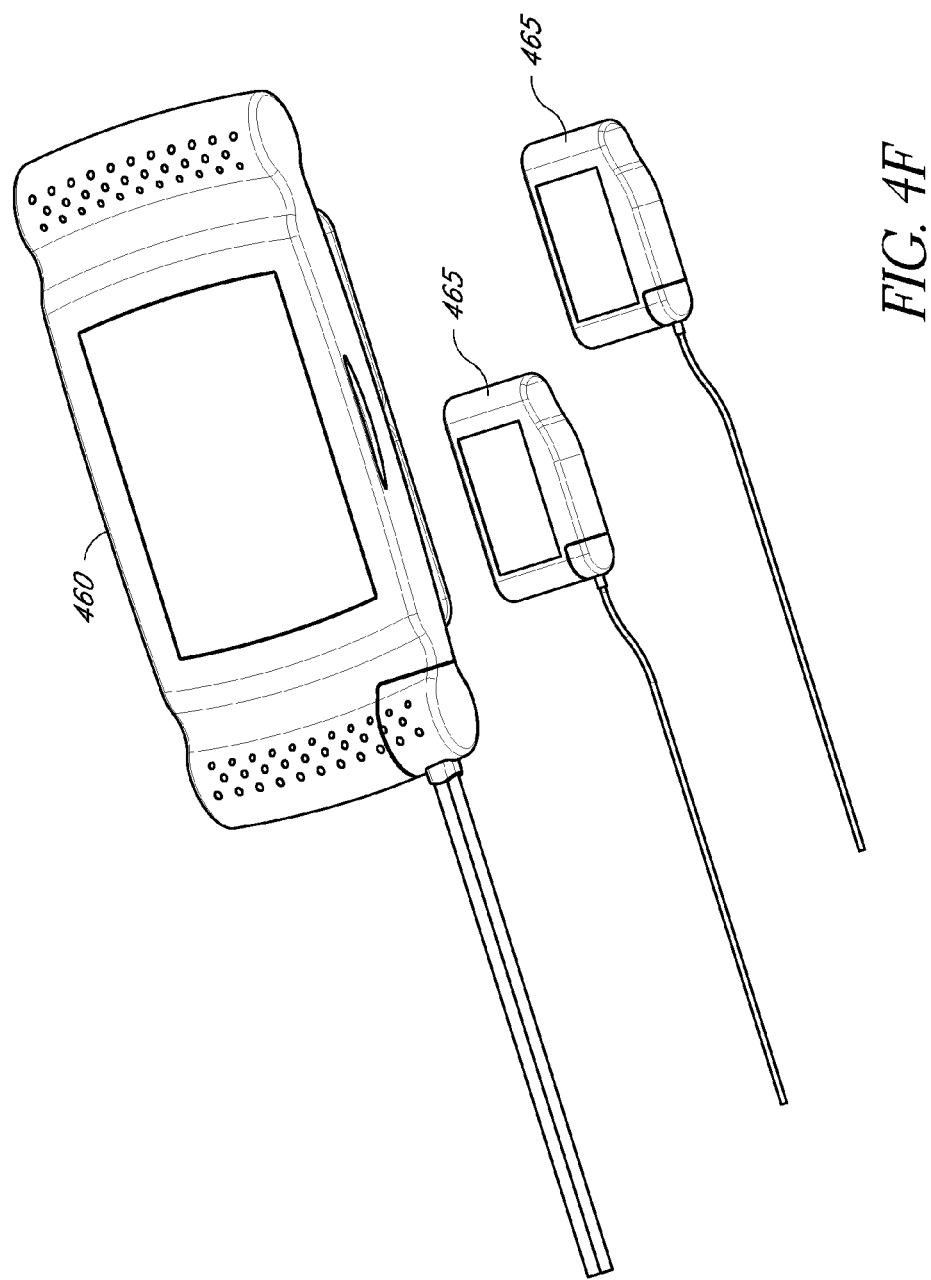

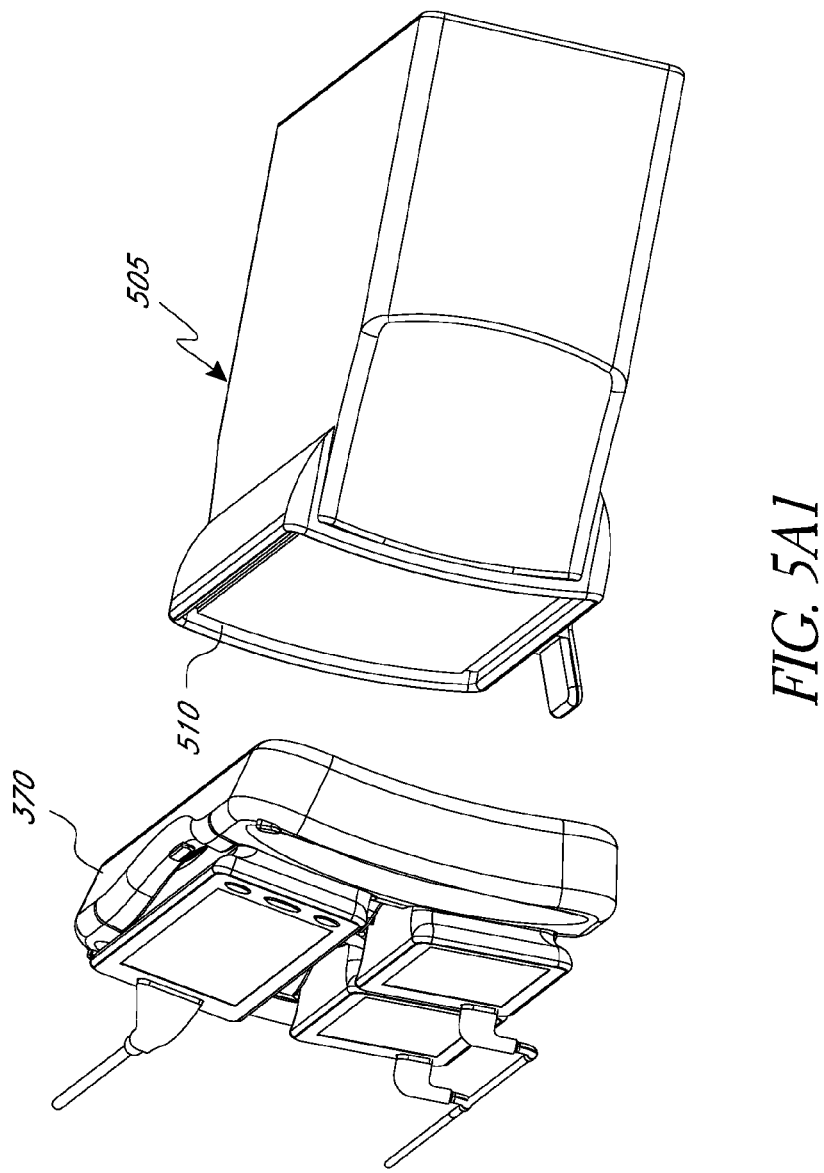
FIG. 5A1

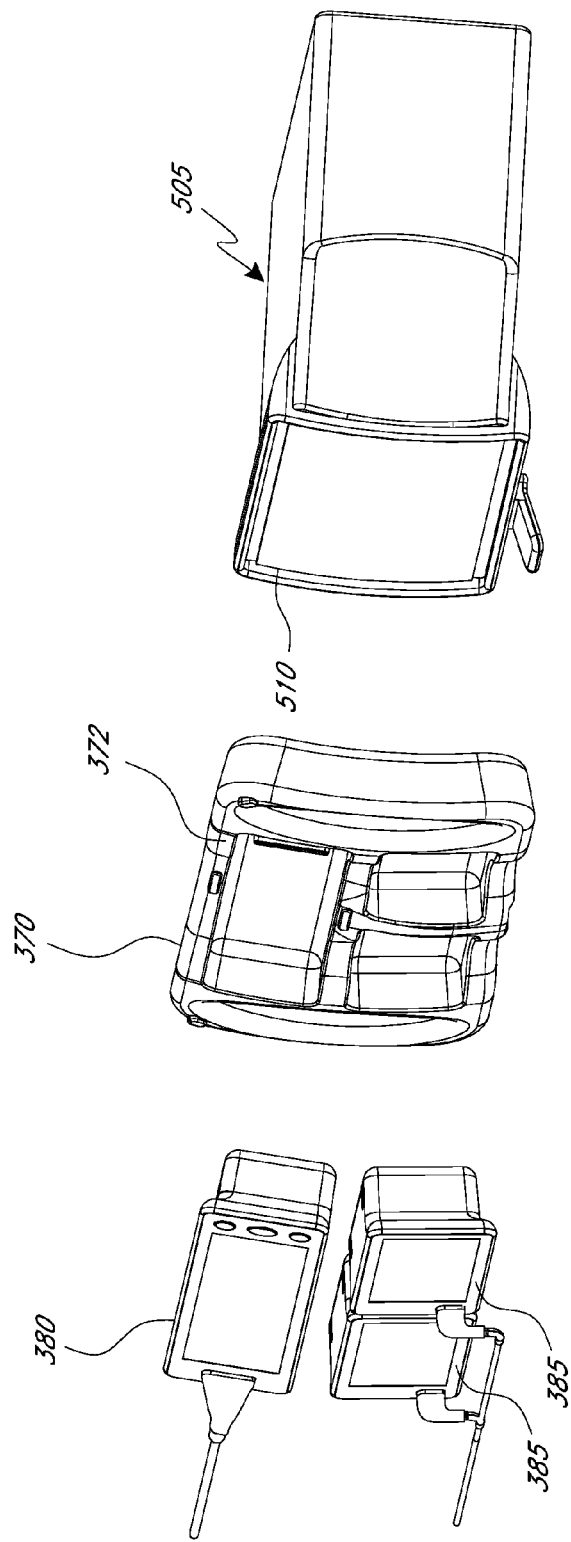
FIG. 5A2

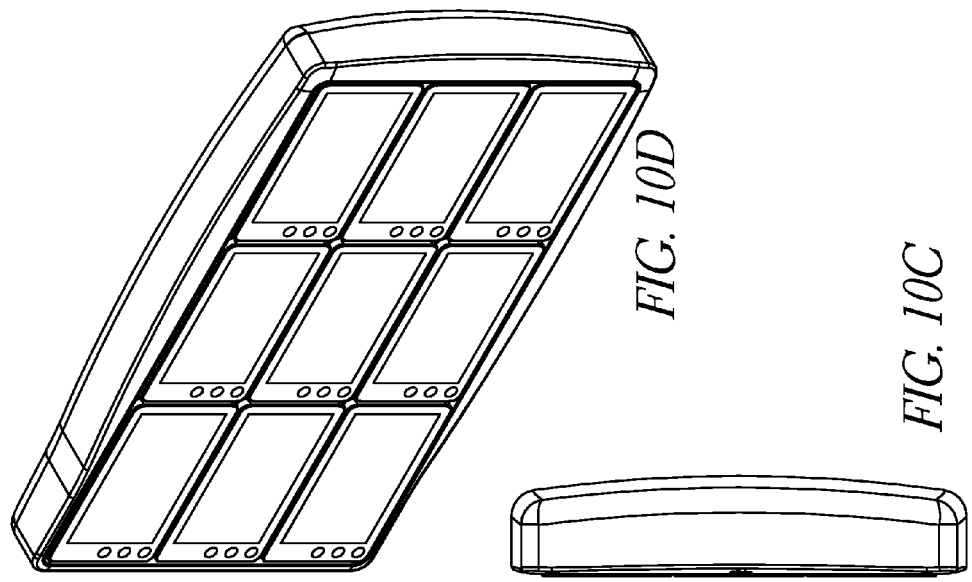
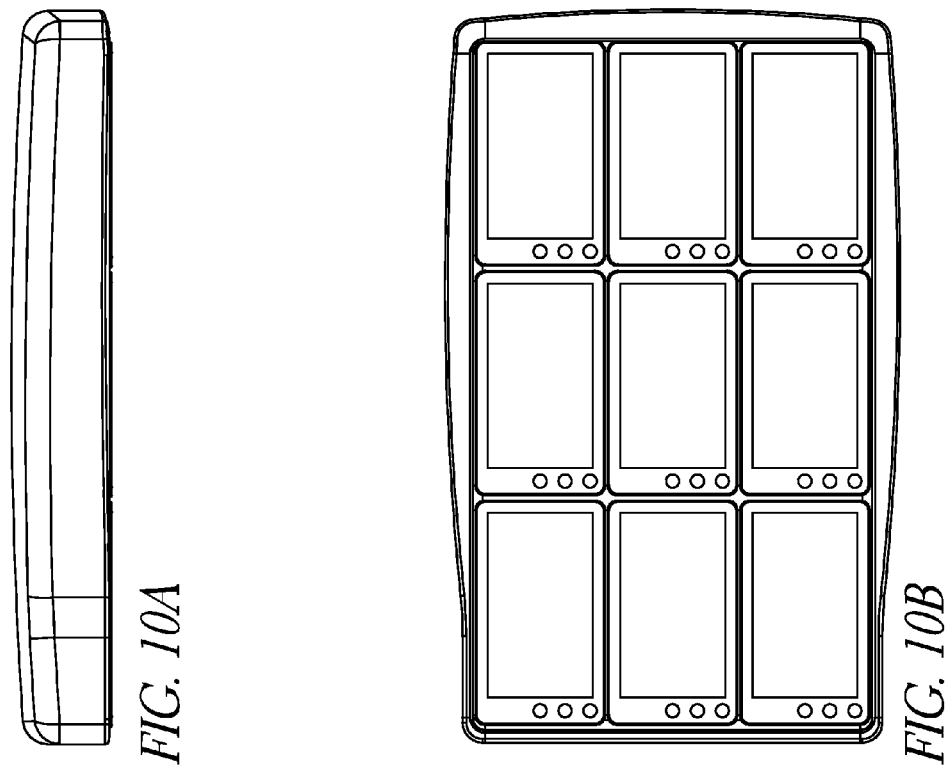

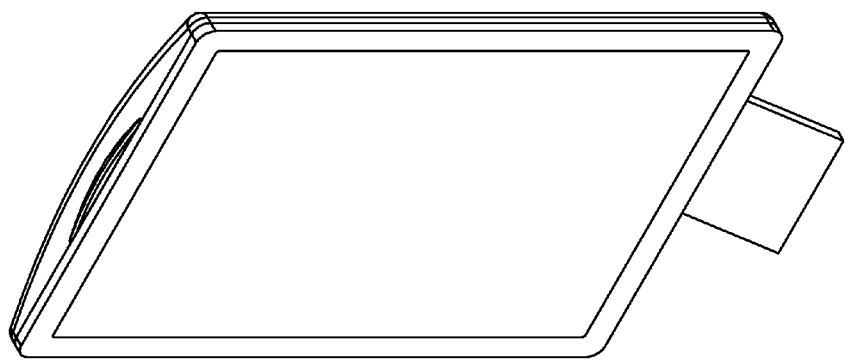
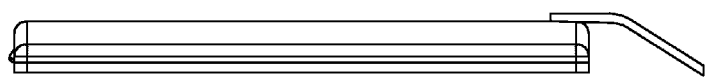
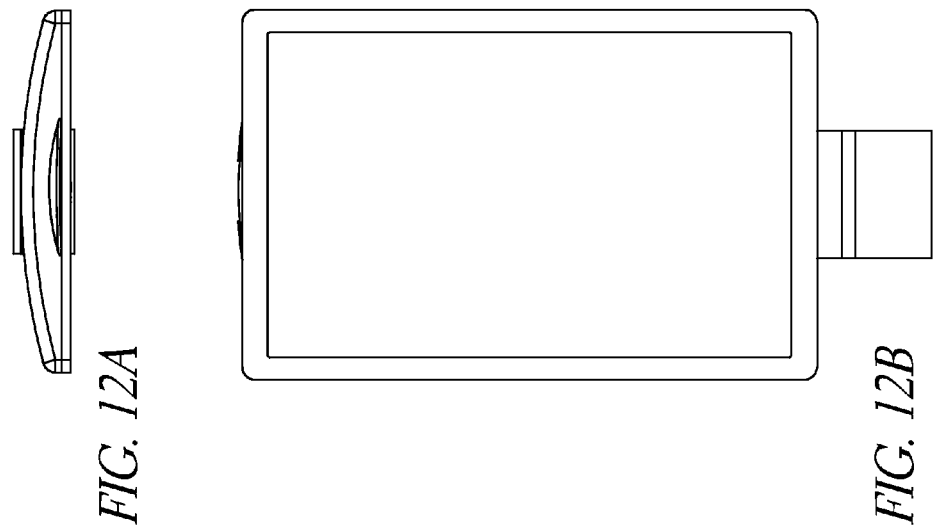

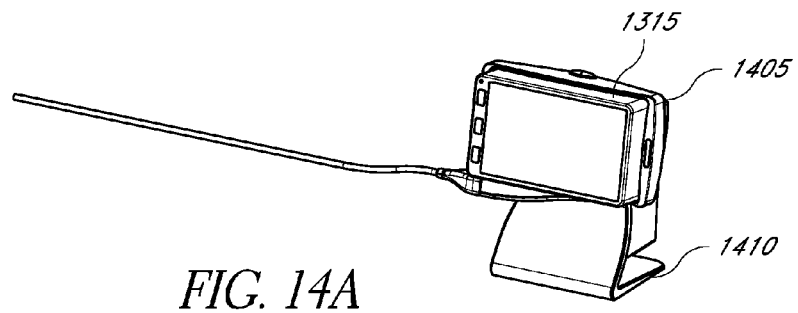
FIG. 14A
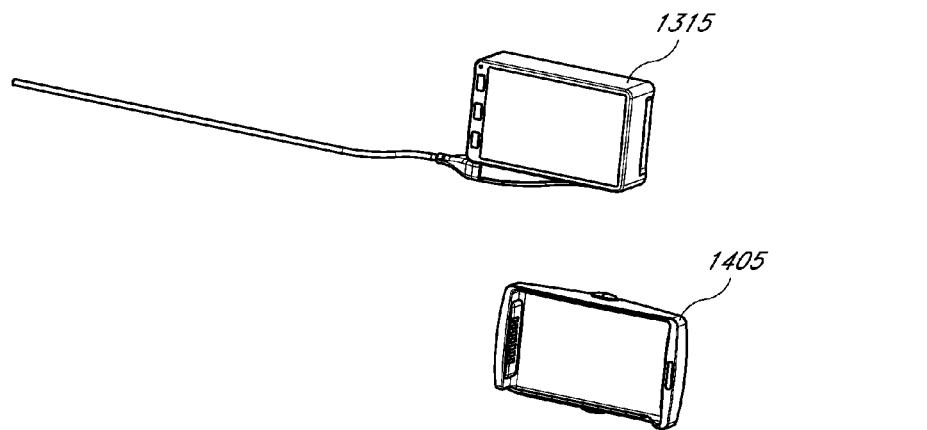
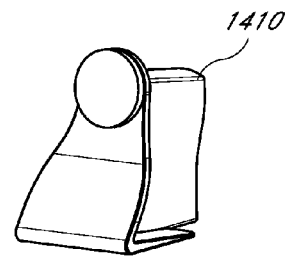
FIG. 14B

MODULAR PATIENT MONITOR

CROSS-REFERENCE TO RELATED APPLICATIONS

This application is a continuation of application Ser. No. 12/973,392, filed Dec. 20, 2010, entitled "Modular Patient Monitor," which claims priority benefit under 35 U.S.C. §119 (e) from U.S. Provisional Application No. 61/405,125, filed Oct. 20, 2010, entitled "Modular Patient Monitor," U.S. Provisional Application No. 61/288,843, filed Dec. 21, 2009, entitled "Acoustic Respiratory Monitor," U.S. Provisional Application No. 61/290,436, filed Dec. 28, 2009, entitled "Acoustic Respiratory Monitor," U.S. Provisional Application No. 61/407,011, filed Oct. 26, 2010, entitled "Integrated Physiological Monitoring System," and U.S. Provisional Application No. 61/407,033, filed Oct. 27, 2010, entitled "Medical Diagnostic and Therapy System," which are incorporated herein by reference in their entirety.

FIELD OF THE DISCLOSURE

The disclosure relates to the field of physiological monitors, and more specifically to a modular monitoring system.

BACKGROUND OF THE DISCLOSURE

Patient monitoring of various physiological parameters of a patient is important to a wide range of medical applications. Oximetry is one of the techniques that has developed to accomplish the monitoring of some of these physiological characteristics. It was developed to study and to measure, among other things, the oxygen status of blood. Pulse oximetry—a noninvasive, widely accepted form of oximetry—relies on a sensor attached externally to a patient to output signals indicative of various physiological parameters, such as a patient's constituents and/or analytes, including for example a percent value for arterial oxygen saturation, carbon monoxide saturation, methemoglobin saturation, fractional saturations, total hematocrit, billirubins, perfusion quality, or the like. A pulse oximetry system generally includes a patient monitor, a communications medium such as a cable, and/or a physiological sensor having light emitters and a detector, such as one or more LEDs and a photodetector. The sensor is attached to a tissue site, such as a finger, toe, ear lobe, nose, hand, foot, or other site having pulsatile blood flow which can be penetrated by light from the emitters. The detector is responsive to the emitted light after attenuation by pulsatile blood flowing in the tissue site. The detector outputs a detector signal to the monitor over the communication medium, which processes the signal to provide a numerical readout of physiological parameters such as oxygen saturation (SpO2) and/or pulse rate.

High fidelity pulse oximeters capable of reading through motion induced noise are disclosed in U.S. Pat. Nos. 7,096,054, 6,813,511, 6,792,300, 6,770,028, 6,658,276, 6,157,850, 6,002,952 5,769,785, and 5,758,644, which are assigned to Masimo Corporation of Irvine, Calif. ("Masimo Corp.") and are incorporated by reference herein. Advanced physiological monitoring systems can incorporate pulse oximetry in addition to advanced features for the calculation and display of other blood parameters, such as carboxyhemoglobin (HbCO), methemoglobin (HbMet), total hemoglobin (Hbt), total Hematocrit (Hct), oxygen concentrations, glucose concentrations, blood pressure, electrocardiogram data, temperature, and/or respiratory rate as a few examples. Typically, the physiological monitoring system provides a numerical readout of and/or waveform of the measured parameter.

Advanced physiological monitors and multiple wavelength optical sensors capable of measuring parameters in addition to SpO2, such as HbCO, HbMet and/or Hbt are described in at least U.S. patent application Ser. No. 11/367,013, filed Mar. 1, 2006, entitled Multiple Wavelength Sensor Emitters and U.S. patent application Ser. No. 11/366,208, filed Mar. 1, 2006, entitled Noninvasive Multi-Parameter Patient Monitor, assigned to Masimo Laboratories, Inc. and incorporated by reference herein. Pulse oximetry monitors and sensors are described in U.S. Pat. No. 5,782,757 entitled Low Noise Optical Probes and U.S. Pat. No. 5,632,272 entitled Signal Processing Apparatus, both incorporated by reference herein. Further, noninvasive blood parameter monitors and optical sensors including Rainbow™ adhesive and reusable sensors and RAD-57™ and Radical-7™ monitors capable of measuring SpO2, pulse rate, perfusion index (PI), signal quality (SiQ), pulse variability index (PVI), HbCO and/or HbMet, among other parameters, are also commercially available from Masimo Corp. Acoustic respiration sensors and monitors are described in U.S. Pat. No. 6,661,161 entitled Piezoelectric Biological Sound Monitor with Printed Circuit Board and U.S. patent application Ser. No. 11/547,570 filed Jun. 19, 2007 entitled Non-Invasive Monitoring of Respiration Rate, Heart Rate and Apnea, both incorporated by reference herein.

SUMMARY OF THE DISCLOSURE

A modular patient monitor provides a multipurpose, scalable solution for various patient monitoring applications. In an embodiment, a modular patient monitor utilizes multiple wavelength optical sensor and/or acoustic sensor technologies to provide blood constituent monitoring and acoustic respiration monitoring (ARM) at its core, including pulse oximetry parameters and additional blood parameter measurements such as carboxyhemoglobin (HbCO) and methemoglobin (HbMet).

Expansion modules provide measurement and/or processing of measurements for blood pressure BP, blood glucose, electrocardiography (ECG), CO2, depth of sedation and cerebral oximetry to name a few. The modular patient monitor is advantageously scalable in features and cost from a base unit to a high-end unit with the ability to measure multiple parameters from a variety of sensors. In an embodiment, the modular patient monitor incorporates advanced communication features that allow interfacing with other patient monitors and medical devices.

Aspects of the present disclosure also include a transport dock for providing enhanced portability and functionally to handheld monitors. In an embodiment, the transport dock provides one or more docking interfaces for placing monitoring components in communication with other monitoring components. In an embodiment, the transport dock attaches to the modular patient monitor.

The modular patient monitor is adapted for use in hospital, sub-acute and general floor standalone, multi-parameter measurement applications by physicians, respiratory therapists, registered nurses and other trained clinical caregivers. It can be used in the hospital to interface with central monitoring and remote alarm systems. It also can be used to obtain routine vital signs and advanced diagnostic clinical information and as an in-house transport system with flexibility and portability for patient ambulation. Further uses for the modular patient monitor can include clinical research and other data collection.

BRIEF DESCRIPTION OF THE DRAWINGS

Throughout the drawings, reference numbers may be reused to indicate correspondence between referenced elements. The drawings are provided to illustrate embodiments of the disclosure described herein and not to limit the scope thereof.

FIGS. 3A-3B illustrate perspective views of an embodiment of a transport dock;

FIGS. 4E-4F illustrate perspective and exploded views, respectively, of a monitoring tablet embodiment having multiple expansion slots;

FIGS. 5A1-5E illustrate docking station embodiments capable of receiving a transport dock, monitoring tablet, and/or handheld monitor;

FIGS. 10A-E are top, front, side, perspective and exploded views, respectively, of a 3×3 rack embodiment with mounted display modules;

FIGS. 12A-D are top, front, side and perspective views, respectively, of a large display and display bracket;

FIGS. 14A-B illustrates an embodiment of the monitor module of FIG. 13A-13B used in combination with a single port dock.

DETAILED DESCRIPTION

Figure 1A:
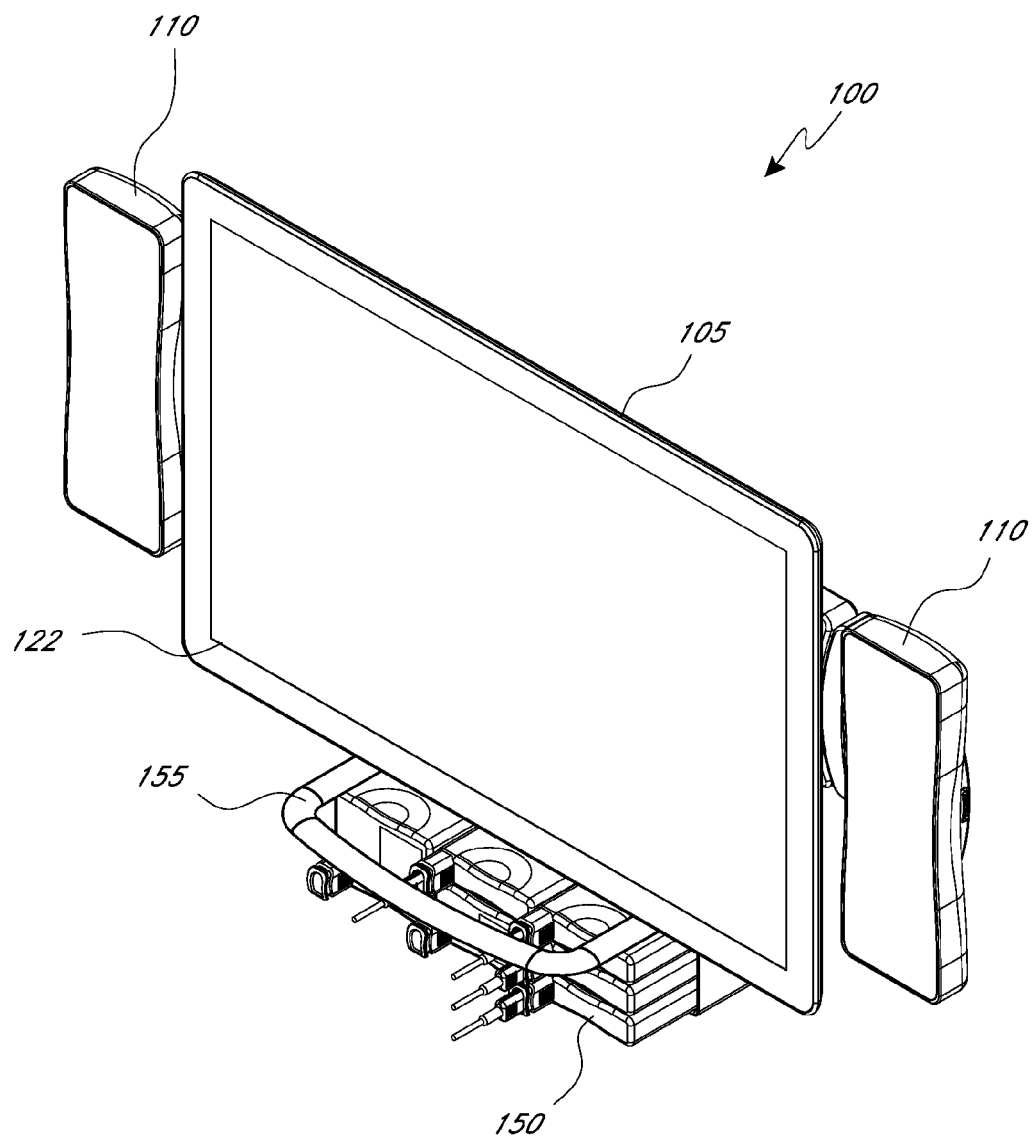
FIGS. 1A-1C illustrate front and rear perspective views and an exploded view of an embodiment of a modular patient monitor 100 having a modular configuration.
Figure 1B:
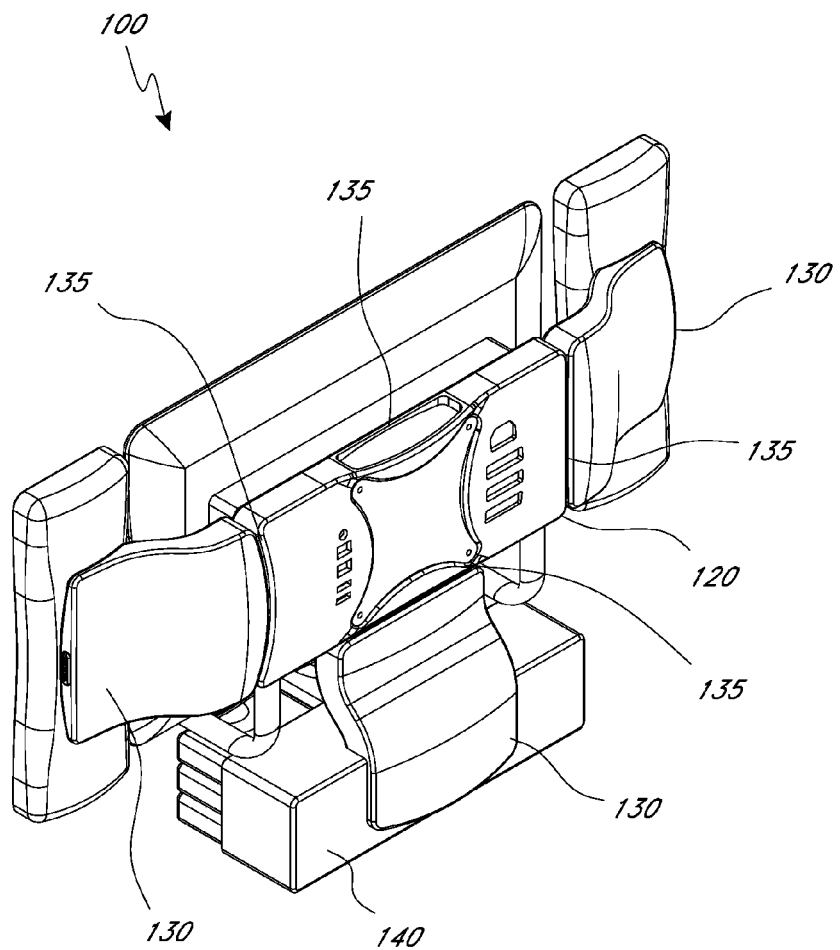
Figure 3A:
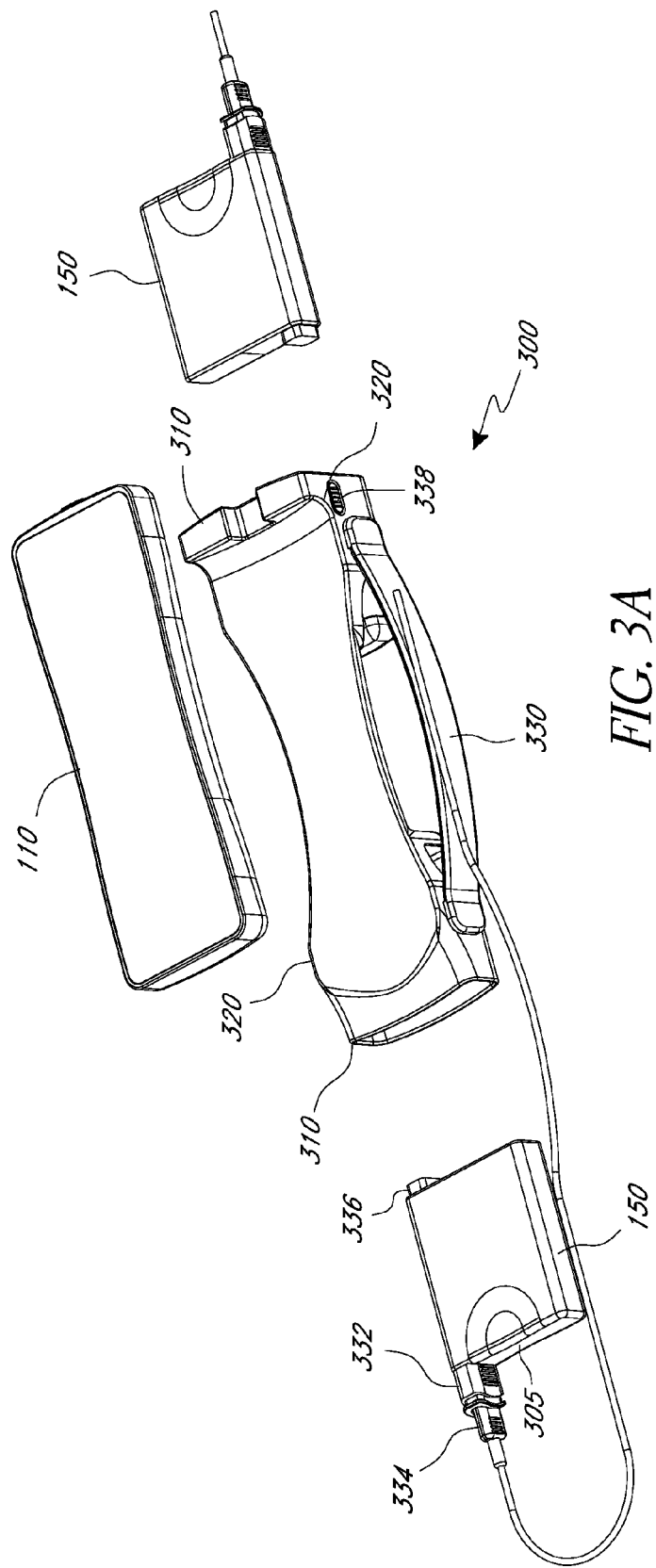

FIGS. 1A and 1B illustrate front and rear views of an embodiment of a modular patient monitor 100 having a modular configuration, one or more handheld 110 units and a configurable docking station 120. FIG. 3A illustrates an exploded view of the patient monitor 100 embodiment. The docking station 120 can include a primary patient monitor 105 integrated with the docking station or that attaches mechanically and/or electrically to the docking station via a docking port. In one embodiment, the docking station does not include a primary patient monitor 105.

One or more handheld monitoring devices can attach mechanically and/or electrically with the docking station 120 via one or more docking ports 135. In one embodiment, mechanical attachment is accomplished through a releasable mechanism, such as locking tabs, pressure fit, hooks, clips, a spring lock or the like. In one embodiment, the docking ports 135 provide a data interface, for example, through its electrical connection. In one embodiment, the electrical connection can provide power to the monitoring device. The handheld 110 docks into a docking arm 130 of the docking station 120, providing the modular patient monitor 100 with additional functionality. In particular, the handheld 110 can provide a specific set of clinically relevant parameters. For example, the handheld 110 supports various parameters that are configured to specific hospital environments and/or patient populations including general floor, OR, ICU, ER, NICU, to name a few. In one embodiment, docking the handheld 110 into the docking station 120 allows access to additional available parameters and provides increased connectivity, functionality and/or a larger display 122. A multi-monitor patient monitor is described in U.S. patent application Ser. No. 12/641,087 titled Modular Patient Monitor, filed Dec. 17, 2009, incorporated by reference herein in its entirety.

In one embodiment, the docking station 120 includes a plurality of docking ports 135 of identical or standard size, interface, and/or configuration. Each docking port can accept different monitoring components with a corresponding standard connector. In one embodiment, different types of monitoring components, such as a handheld monitor 110 or module dock 140, can be interchangeably connected to different docking ports 135. For example, in a first configuration, a first docking port receives the handheld monitor 110 and a second docking port receives the module dock 140, while in a second configuration, the first docking port receives the module dock 140 and the second docking port receives the handheld monitor 110. By providing interchangeable docking ports, users of the modular patient monitor 100 have greater ability to customize the monitor 100 according to their needs. For example, if more displays are needed then additional docking ports can receive displays or handheld monitors but if more parameters are desired or need to be monitored, then additional docking ports can receive module docks and/or expansion modules. In one embodiment, docking ports 135 incorporate USB, IEEE 1394, serial, and/or parallel connector technology.

A docking arm 130 can be detachably connected or integrated with the docking station and/or monitoring component, such a handheld monitor 110 or module dock. In one embodiment, a docking arm 130 attaches mechanically and/or electrically to a handheld monitor 110 on one end and attaches mechanically and/or electrically to a docking port 135 of the docking station 120 on another end. In one embodiment, the docking arm 130 is configured to orient the display of the handheld monitor 110 in a particular orientation. For example, the docking arm 130 can orient the handheld monitor 110 in the same direction as a main display 122 or can angle the handheld monitor 110 in order to display parameters in other directions. In some embodiments, the handheld monitor 110 may be oriented at an angle (e.g. 30, 60, 90 degrees, or the like) from the main display 122, vertically, horizontally, or in a combination of directions. The handheld monitor 100 can be oriented at an angle towards the front or back of the main display 122. In one embodiment, the docking arm 130 is movable and configurable to a variety of orientations. In one embodiment, the docking arm 130 comprises a swivel joint, ball joint, rotating joint, or other movable connector for allowing the docking arm 130 to rotate, twist, or otherwise move an attached monitor 110. For example, the movable connector can rotate on one or more axis, allowing the attached monitor 110 to be oriented in multiple directions. In some embodiments, monitoring components can be directly attached to the docking station without using a docking arm 130.

In the illustrated embodiment of FIGS. 1A and 1B, the docking station 120 is rectangular shaped, having a display on one side, a mounting connector on the opposite side, and four docking ports 135 on the top, bottom, and side edges of the docking station 120. In other embodiments, additional or fewer docking ports 135 can be included on the docking station 120. In some embodiments, the docking ports 135 can provide electrical and/or mechanical connections to handheld monitors 110, module docks 140 with one or more module ports, expansion modules 150 and/or other monitoring components. The monitoring components can attach to a docking port 135 via a docking arm 130 or directly to the port 135. For example, the docking station 120 can include an expansion module 150 or a module dock 140 that accepts plug-in expansion modules 150 for monitoring additional parameters or adding additional monitoring technologies. For example, an expansion module 150 can enable monitoring of electroencephalography (EEG), blood pressure (BP), ECG, temperature, and/or cardiac output. In one embodiment, measurements taken by the monitor are processed by the expansion module. In some embodiments, the expansion module provides attachments for sensors and receives measurements directly from the sensors.

In one embodiment, the module dock 140 functions as a stand for the modular patient monitor 100. In another embodiment, the stand is independent of the module dock 140. In one embodiment, the modular patient monitor 100 provides standalone multi-parameter applications, and the handheld 110 is detachable to provide portability for patient ambulation and in-house transport.

In one embodiment, the module dock 140 provides an interface for expansion modules 150, provides charging for expansion modules 150, and/or interconnects multiple expansion modules by providing a communications medium for data communications between expansion modules and/or other components. For example, the module dock 140 can provide a data interface with a patient monitor or docking station 120, allowing data to be transmitted to and from the expansion modules. In one embodiment, the module dock 140 operates independently of the docking station 120. In one embodiment, the module dock includes a wireless transmitter and/or receiver for communicating wirelessly with the patient monitor or docking station 120.

The handheld monitor 110 and/or primary patient monitor 105 can provide pulse oximetry parameters including oxygen saturation ($SpO_2$), pulse rate (PR), perfusion index (PI), signal quality (SiQ) and a pulse waveform (pleth), among others. In an embodiment, the handheld 110 and/or primary patient monitor 105 also provides measurements of other blood constituent parameters that can be derived from a multiple wavelength optical sensor, such as carboxyhemoglobin (HbCO) and methemoglobin (HbMet). In one embodiment, the handheld 110 and/or primary patient monitor 105 has a color display, user interface buttons, an optical sensor port and a speaker. The handheld 110 and/or primary patient monitor 105 can include external I/O such as a bar code reader and bedside printer connectivity. The handheld 110 and/or primary patient monitor 105 can display additional parameters, such as $Sp_vO_2$, blood glucose, lactate to name a few, derived from other noninvasive sensors such as acoustic, fetal oximetry, blood pressure and ECG sensors to name a few. In an embodiment, the handheld unit 110 and/or primary patient monitor 105 has an active matrix (TFT) color display, an optional wireless module, an optional interactive touchscreen with on-screen keyboard and a high quality audio system. In another embodiment, the handheld 110 is a Radical® or Radical-7™ available from Masimo Corporation, Irvine Calif., which provides Masimo SET® and Masimo Rainbow™ parameters. A color LCD screen handheld user interface is described in U.S. Provisional Patent Application No. 60/846,472 entitled Patient Monitor or User Interface, filed Dec. 22, 2006 and U.S. patent application Ser. No. 11/904,046 entitled Patient Monitor User Interface, filed Sep. 24, 2007, both applications incorporated by reference herein in their entirety.

In an embodiment, controls on the docking station 120 and/or the docked handheld 110 provide controls for the modular patient monitor 100. For example, the controls can included buttons for alarm suspend/silence and mode/enter, a trim knob to toggle thru screen menus, and other controls such as next, up, down or across page navigation, parameter selection and entry, data entry, alarm limit selection and selection of probe-off detection sensitivity. As a secondary control method, the modular patient monitor 100 can include a port for an external keyboard for patient context entry and to navigate the menu. In an embodiment, the docking station has a touch screen, for example, the display 122 or a docked handheld monitor 110 can provide touch screen functionality. In an embodiment, the modular patient monitor 100 has a bar code scanner module adapted to automatically enter patient context data.

The modular patient monitor 100 can include an integral handle 155 for ease of carrying or moving the monitor 100 and dead space for storage for items such as sensors, reusable cables, ICI cable and cuff, $EtCO_2$ hardware and tubing, temperature disposables, acoustic respiratory sensors, power cords and other accessories such as ECG leads, BP cuffs, temperature probes and respiration tapes to name a few. The monitor 100 can operate on AC power or battery power. The modular patient monitor 100 can stand upright on a flat surface or can allow for flexible mounting such as to a monitor arm or mount, an anesthesia machine, bedside table and/or computer on wheels. In one embodiment, the docking station 120 includes a Video Electronics Standards Association (VESA) mount for attaching stands, monitor arms, or other mounting devices.

In one embodiment, the docking station 120 can have its own stand-alone patient monitoring functionality, such as for pulse oximetry, and can operate without an attached handheld monitor 110. The docking station receives patient data and determines measurements to display for a monitored physiological parameter.

One or more of handheld monitors 110 can be docked to the docking station 120. When undocked, the handheld monitor 110 operates independently of the docking station 120. In some embodiments, a particular handheld monitor can be configured to receive patient data and determine parameter measurements to display for a particular physiological parameter, such as, for example, blood pressure, other blood parameters, ECG, and/or respiration. In one embodiment, the handheld monitor can operate as a portable monitor, particularly where only some parameters are desired or need to be measured. For example, the handheld monitor, while providing patient monitoring, can travel with a patient being moved from one hospital room to another or can be used with a patient travelling by ambulance. Once the patient reaches his destination, the handheld monitor can be docked to a docking station at the destination for expanded monitoring.

In some embodiments, when a handheld monitor 110 is docked to the docking station 120, additional parameters can become available for display on the main display 122. Upon receiving additional measurements, the docking station 120 can reorganize and/or resize existing measurements on the display 122 to make room for measurements of the additional parameters. In some embodiments, a user can select which measurements to display, drop, and/or span using the controls on the docking station 120. In some embodiments, the docking station 120 can have an algorithm for selecting measurements to display, drop, and/or span, such as by ranking of measurements or by display templates.

In order to expand display space on the main display 122, measurements can be spanned across the main display 122 and the displays on the handheld monitors 110. In one embodiment, the measurements can be spanned by displaying a partial set of the measurements on the main display 122 and additional measurements on the handheld monitors 110. For example, the main display 122 can display some measurements of a parameter, such as a numerical value, while the handheld monitor 110 displays additional measurements, such as the numerical value and an associated waveform.

Alternatively, measurements can be spanned by mirroring on the main display 122 the handheld monitor display. For example, portions of the main display 122 can display all or some of the measurements on a handheld monitor display, such as a numerical value and a waveform.

In one embodiment, the main display 122 can take advantage of its greater size relative to handheld monitor displays to display additional measurements or to display a measurement in greater detail when measurements of a physiological parameter are spanned. For example, portions of the main display 122 can display numerical values and a waveform while a handheld monitor display shows only a numerical value. In another example, the main display 122 can display a waveform measured over a longer time period than a waveform displayed on the handheld monitor, providing greater detail.

In some embodiments, the main display 122 displays a set of measurements when the modular patient monitor 100 is operating independently (e.g. a numerical value and a waveform), but only a partial set of the measurement when docked to the docking station (e.g. numerical value), thereby freeing up display space on the handheld monitor's display. Instead, the remaining measurements (e.g. waveform) can be displayed on the docking station display. In some embodiments, the partial measurement (e.g. numerical value) on the portable monitor is enlarged to increase readability for a medical professional. In some embodiments, the handheld monitor display can show the partial measurement in greater detail or display an additional measurement.

In some embodiments, data is transmitted between components of the modular patient monitoring system, such as a patient monitor, handheld monitors 110 and/or expansion modules 150 through a data connection. The data can be transferred from one component through the docking station's docking port and then to another component. In one embodiment, a cable can be used to connect an input on one component to an output on another component, for a direct data connection. Data can also be transmitted through a wireless data connection between the docking station 120 and components and/or between individual components. In some embodiments, the docking station can further analyze or process received data before transmitting the data. For example, the docking station can analyze data received from one or more monitors and generate a control signal for another monitor. The docking station can also average, weight and/or calibrate data before transmitting the data to a monitor.

Data from other monitoring components can be used to improve the measurements taken by a particular monitoring component. For example, a brain oximetry monitor or module can receive patient data from a pulse oximetry monitor or module, or vice versa. Such data can be used to validate or check the accuracy of one reading against another, calibrate a sensor on one component with measurements taken from a sensor from another component, take a weighted measurement across multiple sensors, and/or measure the time lapse in propagation of changes in a measured physiological parameter from one part of the body to another, in order, for example, to measure circulation. In one example, a monitor can detect if the patient is in a low perfusion state and send a calibration signal to a pulse oximetry monitor in order to enhance the accuracy of the pulse oximetry measurements. In another example, data from a pulse oximetry monitor can be used as a calibration signal to a blood pressure monitor. Methods and systems for using a non-invasive signal from a non-invasive sensor to calibrate a relationship between the non-invasive signal and a property of a physiological parameter are described in U.S. Pat. No. 6,852,083, entitled System and Method of Determining Whether to Recalibrate a Blood Pressure Monitor, issued Feb. 8, 2005, incorporated by reference herein in its entirety. Of course, other information from one monitor of any type can be used to enhance the measurements of another monitor.

Figure 2A:
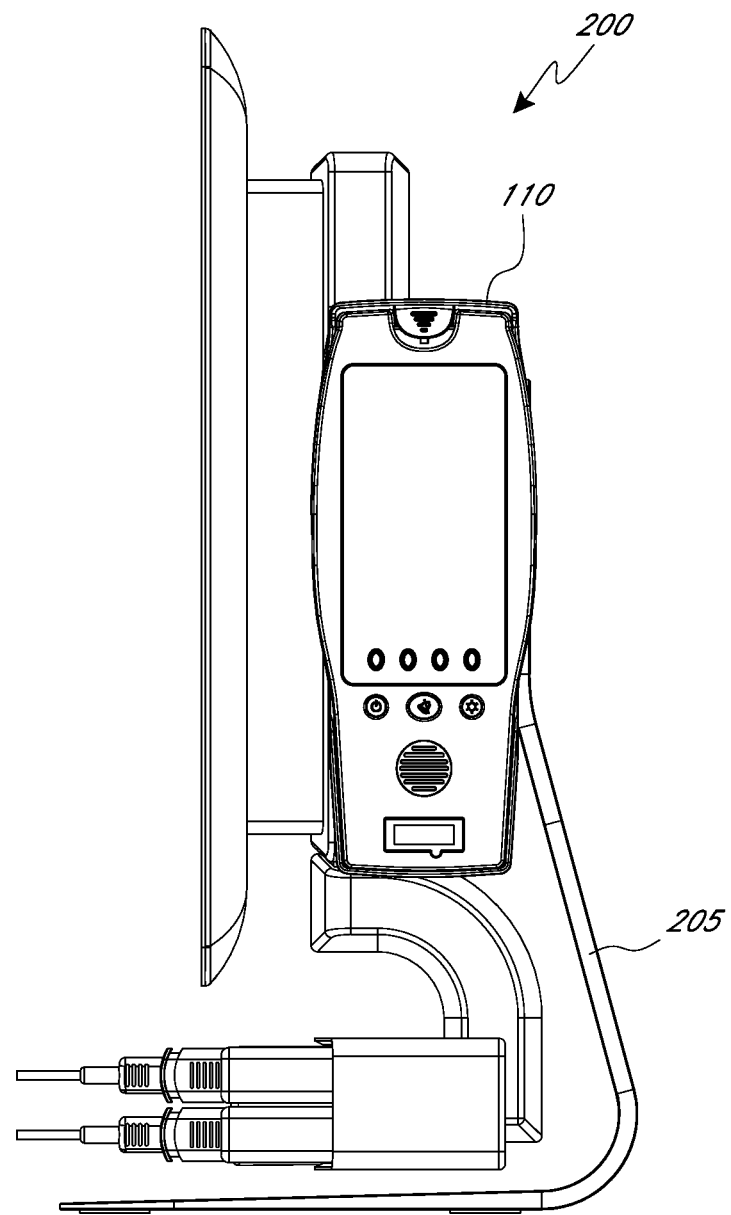
FIGS. 2A-2B illustrate side and rear views of a modular patient monitor embodiment 200 having an attached stand.
Figure 2B:
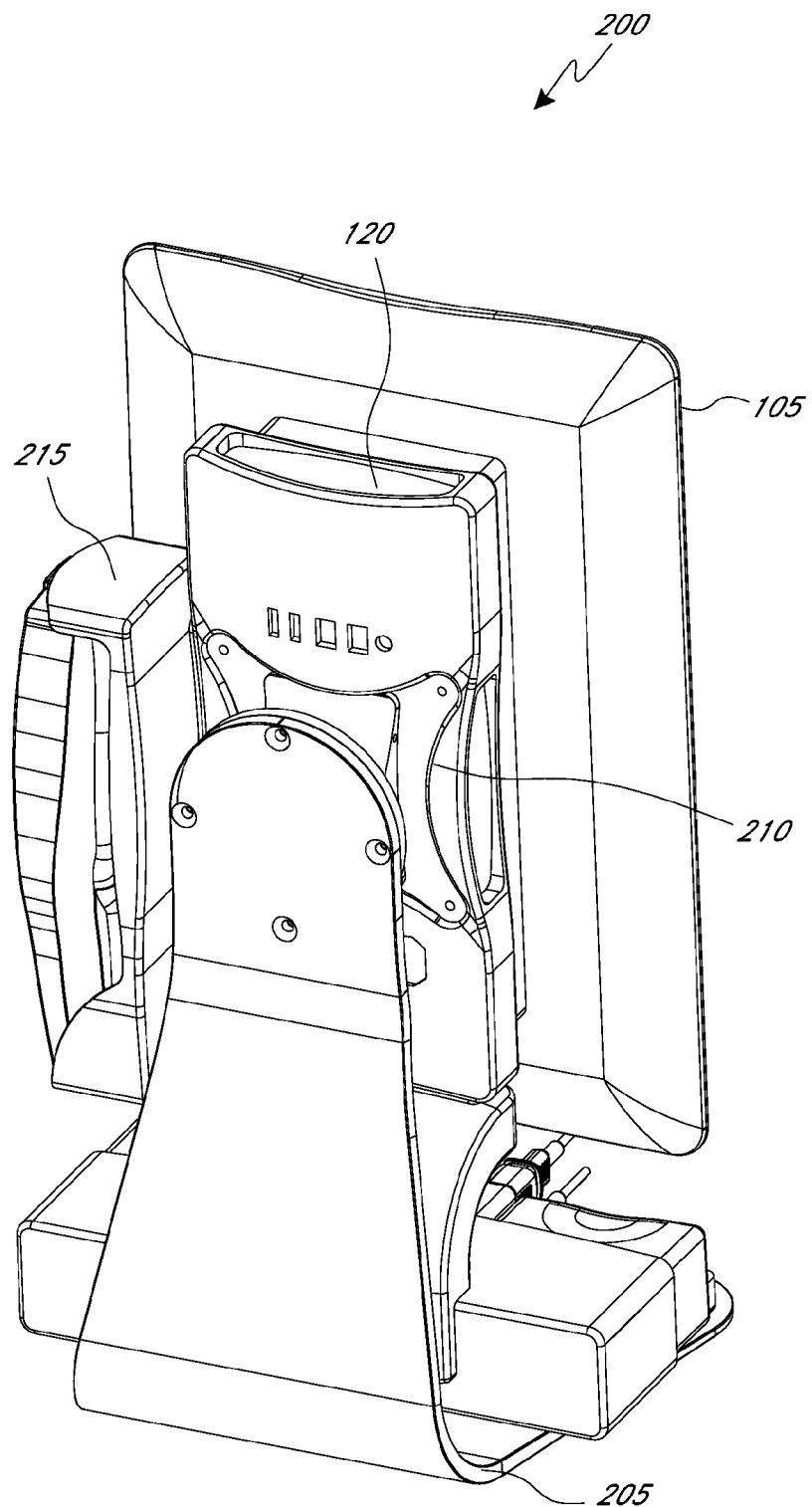

FIGS. 2A-2B illustrate side and rear views of a modular patient monitor embodiment 200 having an attached stand. In the illustrated embodiment, the stand 205 attaches to the docking station 120 via a mount 210, such as a VESA mount. In FIGS. 2A and 2B, the handheld monitor 110 attaches to a docking arm 215 configured to orient the handheld monitor display at an approximately 90 degree angle to the main display 122. By positioning the handheld 110 in a different orientation than the main display 122, users, such as health professionals, can view the parameters on display from different positions in a location, such as a hospital room or operating room. For example, a surgical team in a first position operating on a patient can view parameters on one display while an anesthesiologist monitoring the patient in a second position can view parameters on the handheld display. In some embodiments, the parameters on the handheld display can be different than the parameters on the main display, for example, where health professionals are concerned with or are monitoring different parameter sets.

Relative to FIGS. 1A and 1B, the main display 122 and stand 205 are configured in portrait mode, where the height of the display is greater than the width, as opposed to landscape mode, where the width of the display is greater than the height. In one embodiment, the main display 122 may be rotated from portrait mode to landscape mode and vice versa.

Figure 2C:
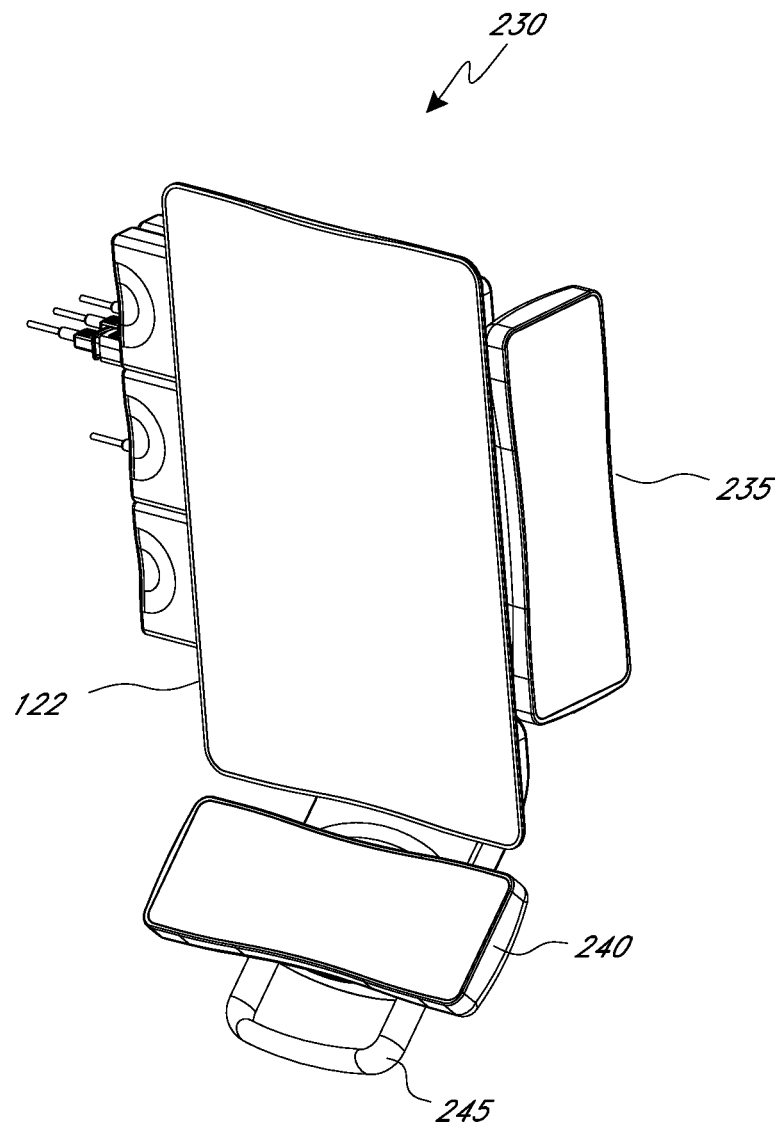
FIGS. 2C-2D illustrate front and rear perspective views of an embodiment of the modular patient monitor having two handheld monitors attached to the docking station with each handheld monitor in a different orientation.
Figure 2D:
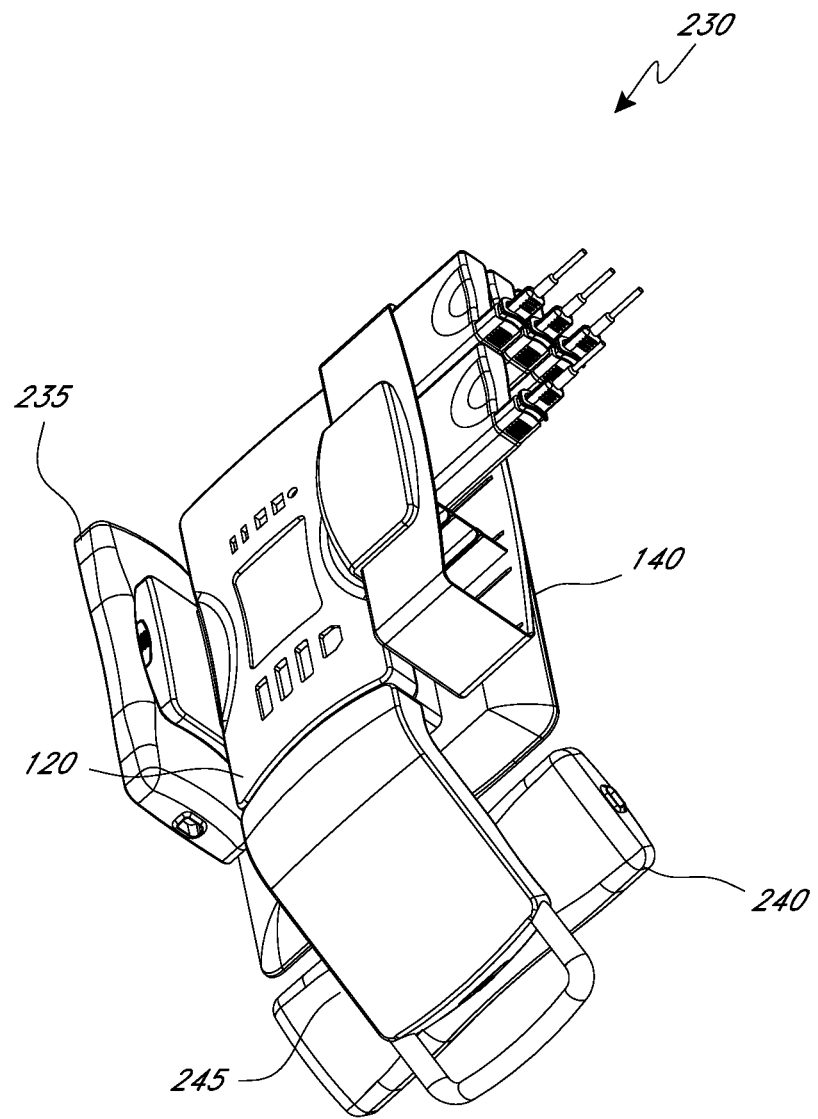

FIGS. 2C and 2D illustrate front and rear perspective views of an embodiment of the modular patient monitor 230 having two handheld monitors 235, 240 attached to the docking station 120 with each handheld monitor in a different orientation. The modular patient monitor 230 can include a module dock 140 attached to the docking station 120.

In the illustrated embodiment, the first handheld monitor 235 is facing a different direction than the main display 122, and a second handheld monitor 240 faces approximately the same direction as the main display 122 and angled upwards. In one embodiment, the main display 122 is positioned at eye-level of a health professional and the second handheld monitor 240 below the main display 122 is angled upwards towards the view of the health professional. In one embodiment, the second handheld monitor 240 can be placed above the main display 122 and angled downward towards the view of the health professional.

In one embodiment, the second handheld monitor 240 can function as a touch screen input device for the primary monitor when attached to the docking station 120. For example, the handheld monitor 240 can display monitor controls in addition to or instead of parameter values. In one embodiment, a user can select the display mode of the handheld monitor.

In one embodiment, the second handheld monitor 240 is attached to a transport dock 245 having an integrated handle. In one embodiment, the transport dock 245 can attach or detach to a docking port on the docking station and serves as a portable carrier for one or more handheld monitors and/or other monitoring components. Embodiments of the transport dock 245 are described in further detail below.

Figure 2E:
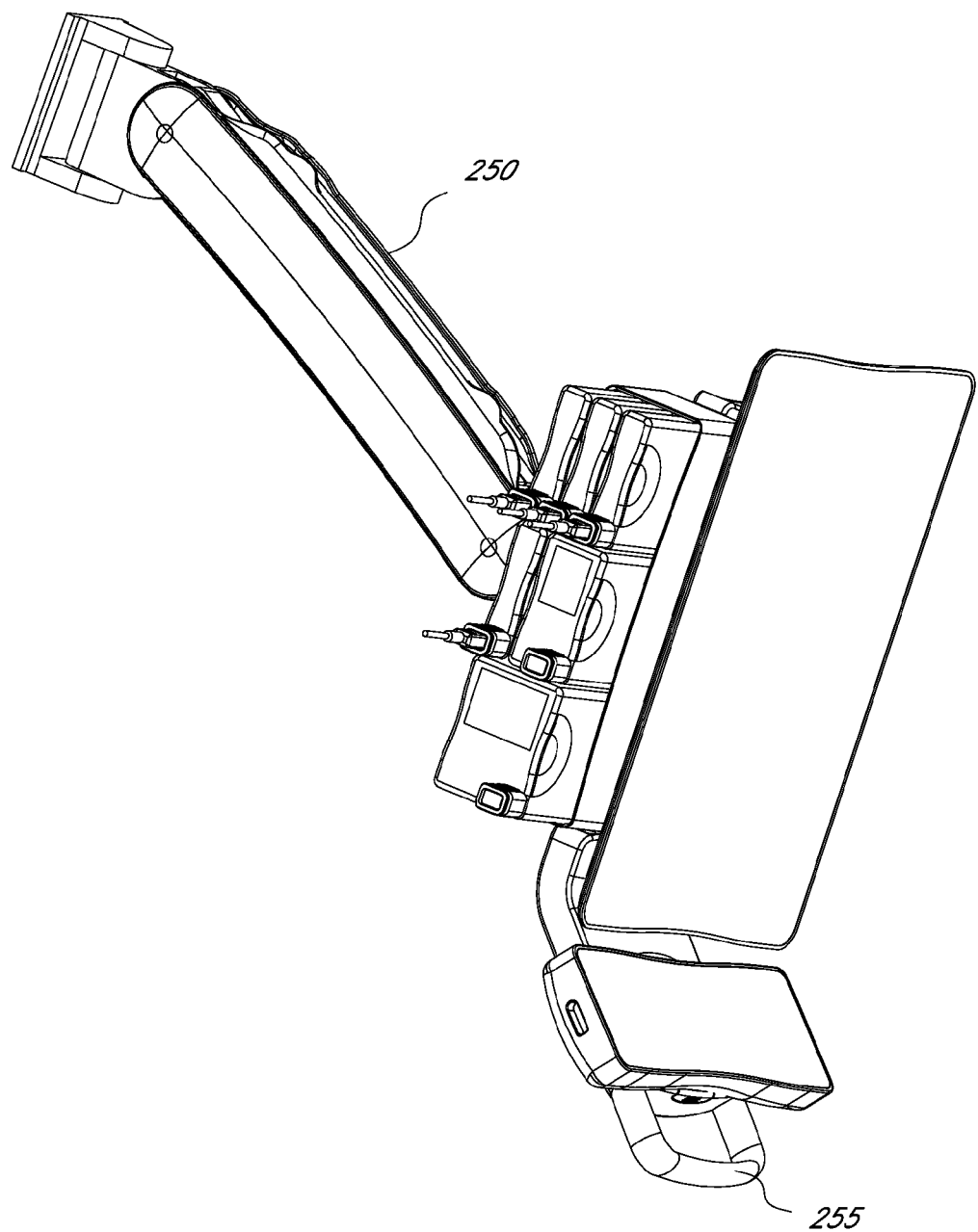
FIGS. 2E-2G illustrate front and rear perspective views and an exploded view of the modular patient monitor embodiment of FIGS. 2C and 2D attached to a mounting arm.
Figure 2F:
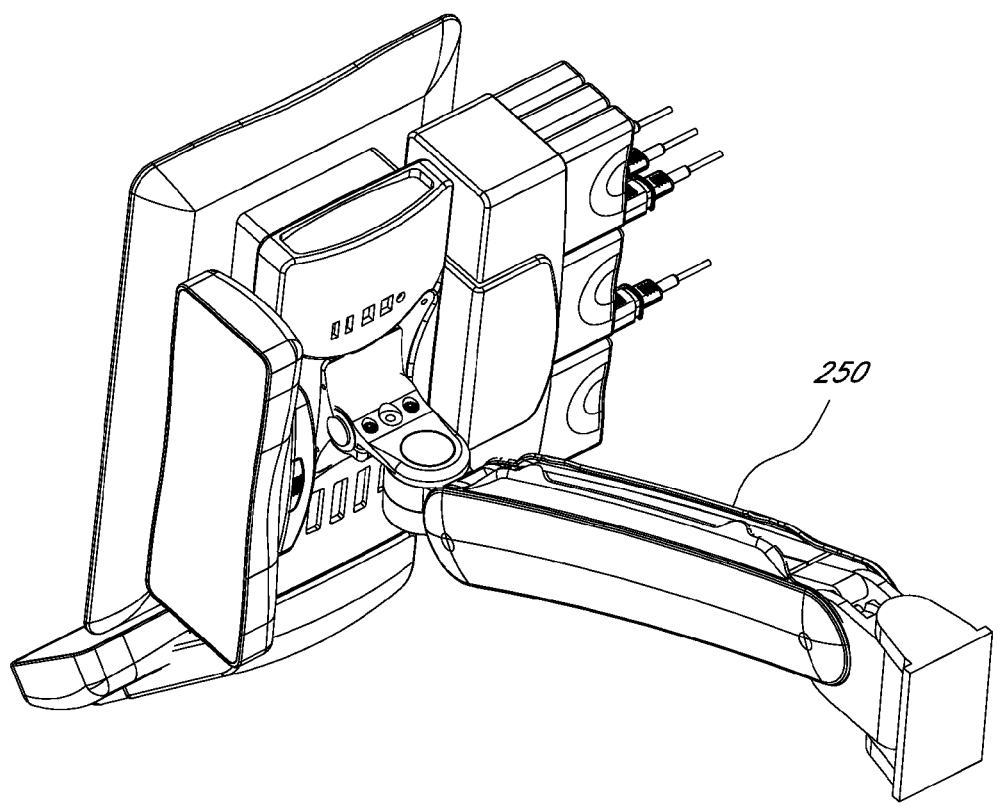
Figure 2G:
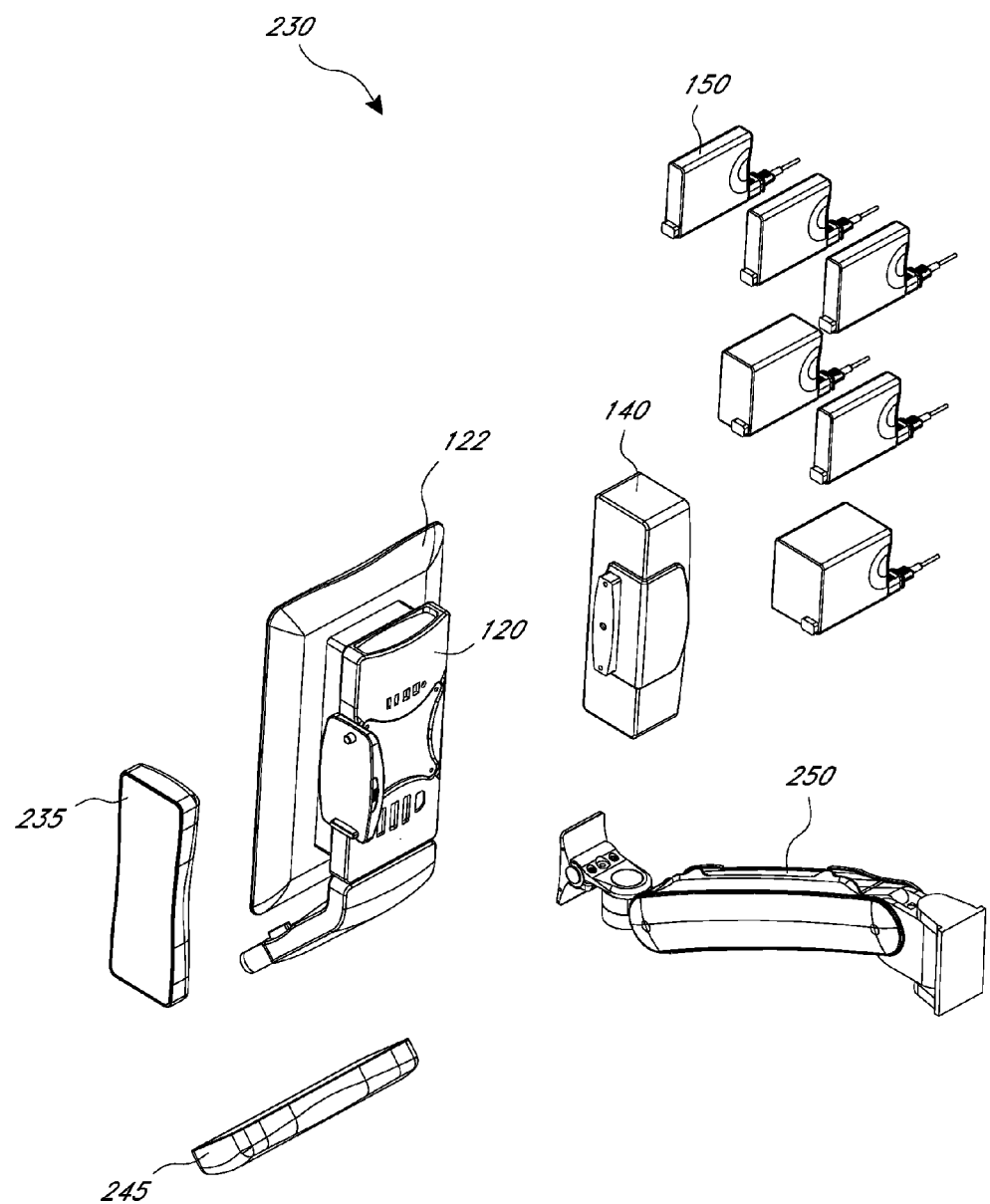

FIGS. 2E and 2F illustrate front and rear perspective views of the modular patient monitor embodiment 230 of FIGS. 2C and 2D attached to a mounting arm 250. In one embodiment, the handle 255 can allow a user to move the patient monitor 230 into different positions and/or orientations. FIG. 2G illustrates an exploded view of the patient monitor 230 embodiment.

In one embodiment, the module dock 140 can receive different sizes of expansion modules. For example, modules can be 1× size 240, 2× size 265 or 3× size 270. In one embodiment, larger modules provide greater measurement capability and/or processing power. For example, a 3× module can measure more parameters, provide more detailed monitoring of a parameter, and/or track more complex parameters relative to a 1× module. In one embodiment, an expansion module can include a display 275 on an exposed portion of the module to display parameter measurements, module status, and/or other information.

Figure 2H:
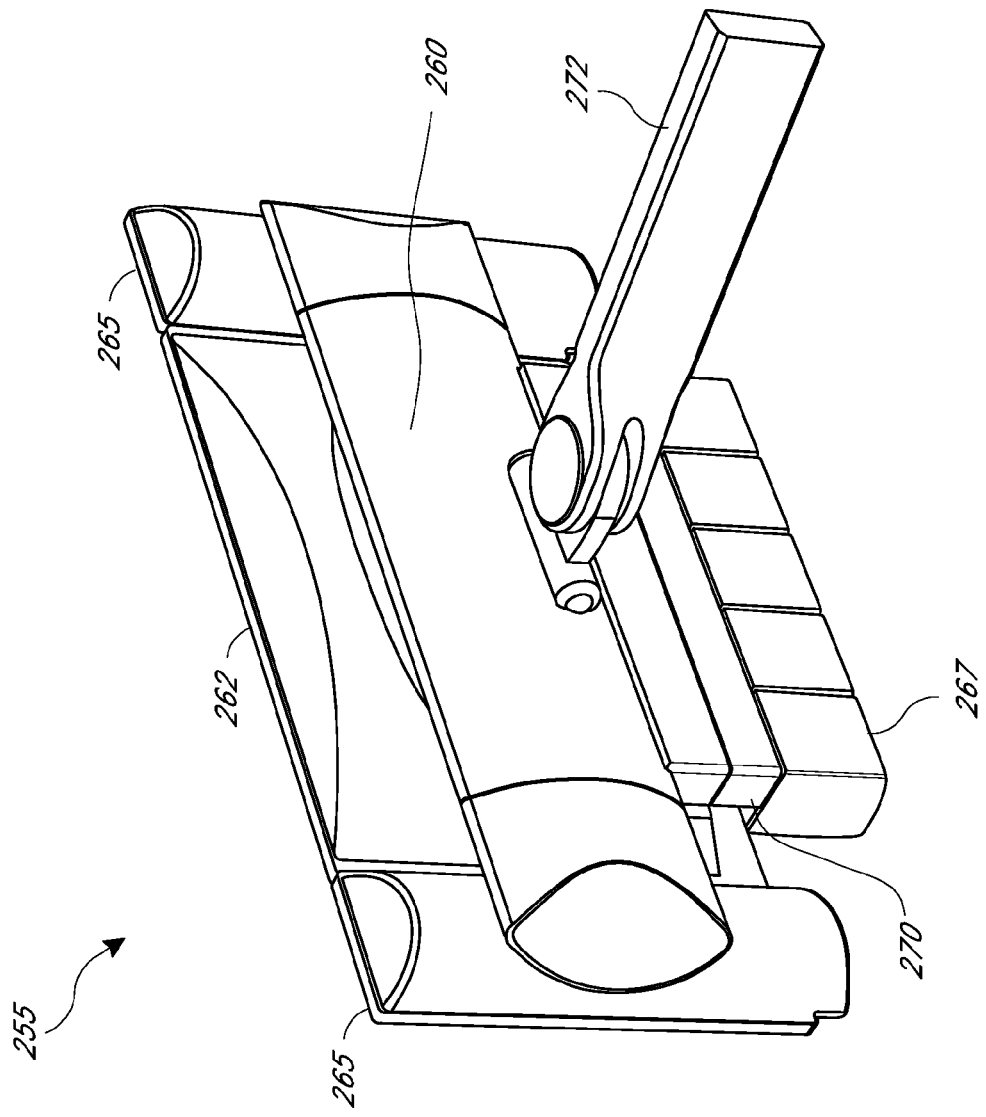
FIGS. 2H-2J illustrate rear perspective, exploded, and side views, respectively, of another embodiment of the modular patient monitor
Figure 2I:
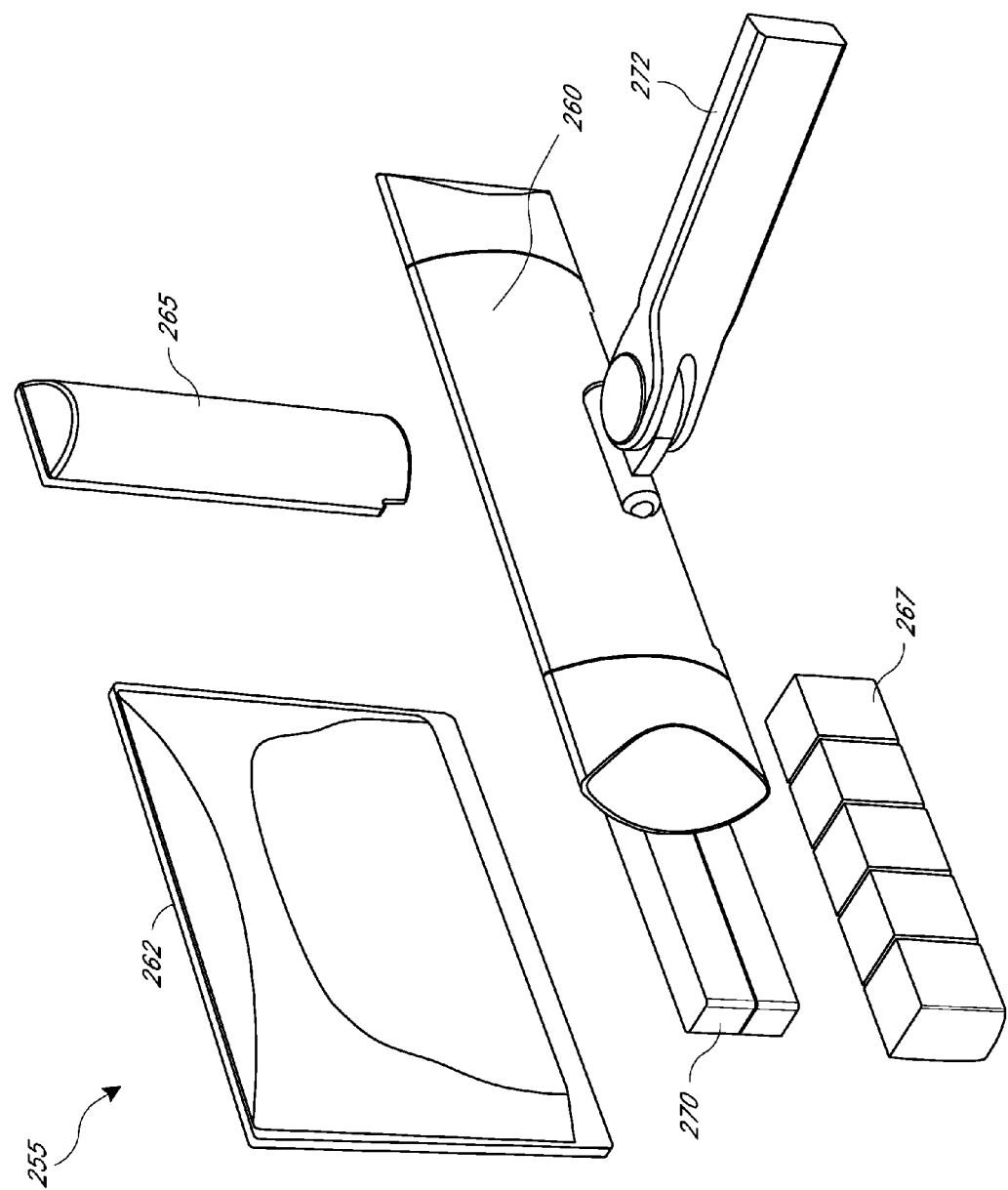
Figure 2J:
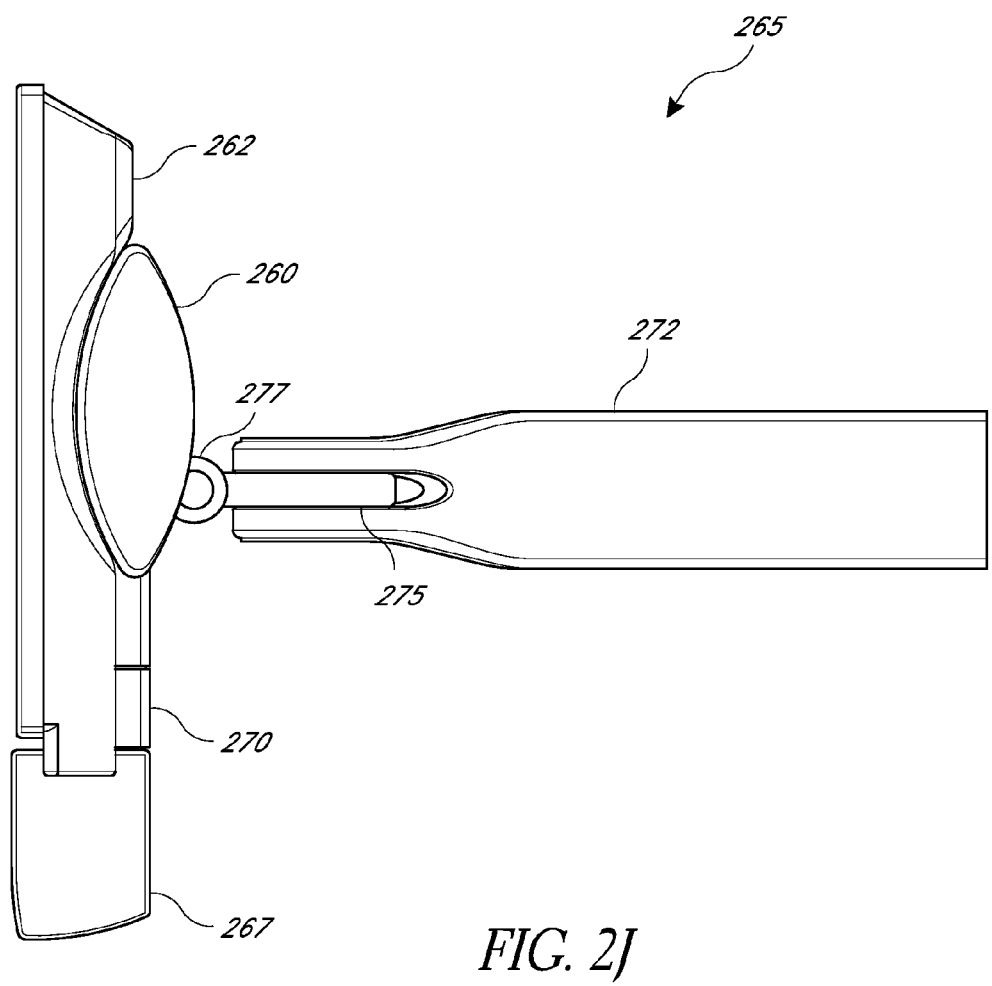
Figure 6:
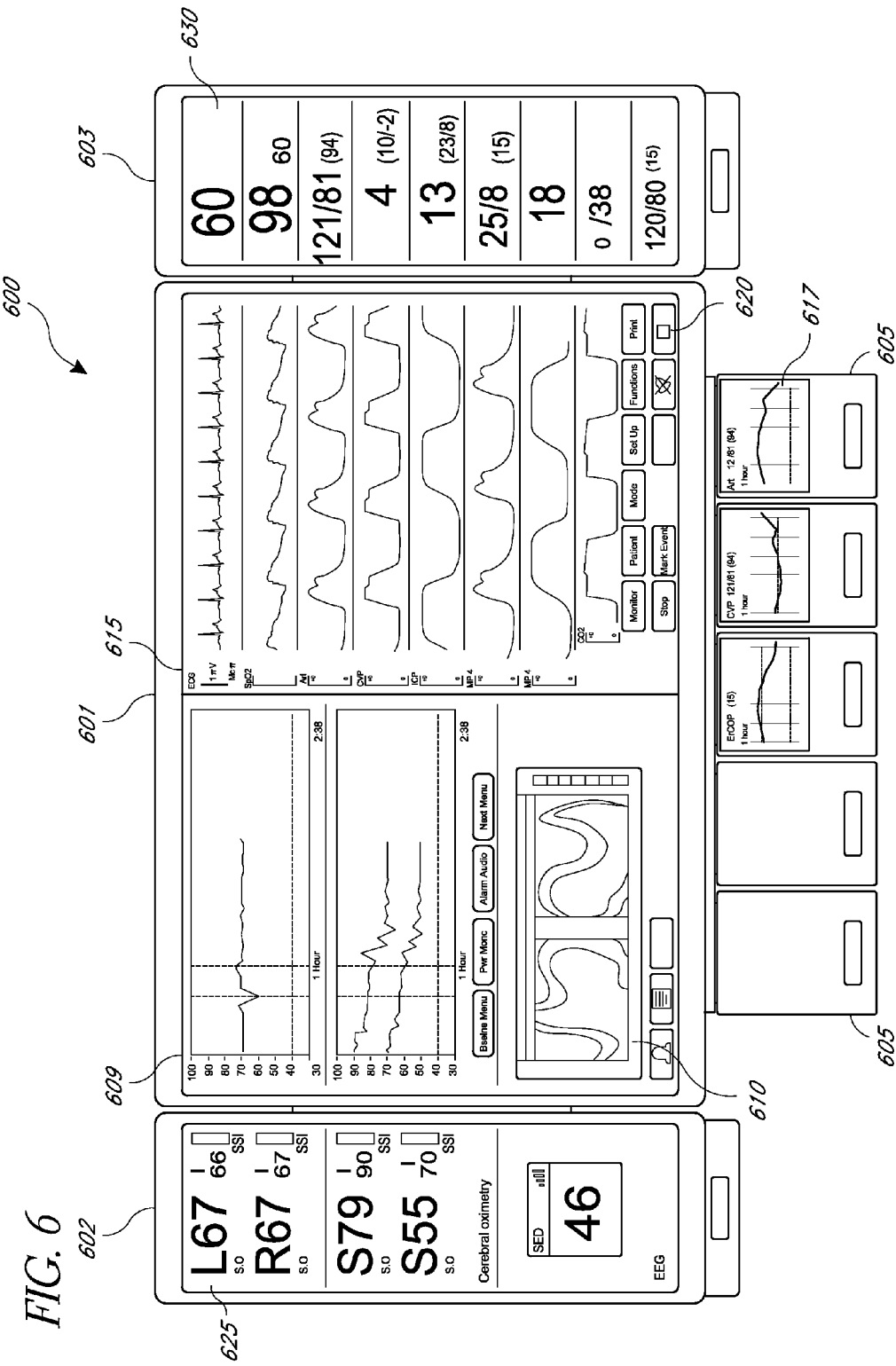
FIG. 6 illustrates a front view of the embodiment of the modular patient monitor of FIGS. 2H-2J, displaying measurements for parameters across multiple displays.

FIGS. 2H-2J illustrate rear perspective, exploded, and side views, respectively, of another embodiment of the modular patient monitor 255. A front view of the embodiment is shown in FIG. 6. In this embodiment, the modular patient monitor 255 includes a docking station 260 with one or more displays 262 and/or portable monitors having displays 265 attached. The display 262 can be integrated with the docking station or detachable. The illustrated docking station 260 is generally elongate with docking mechanisms for one or more displays 262 and/or portable monitors 265 on the front (e.g. user facing side) of the docking station 260. In the illustrated embodiment, the docking station's 260 front surface is a generally convex surface configured to attach to generally concave docking surfaces of the display 262 and/or portable monitors 265. The docking station's rear facing surface can also be generally convex.

A module dock 270 can be integrated or detachably connected to the docking station 260. The module dock 270 can provide mechanical and/or electrical connections to one or more expansion modules 267. In FIGS. 2H, 2I, and 2J, the module dock 270 is attached to the bottom facing side of the docking station; however, other configurations, such as being attached to the sides or the top of the docking station 260, are possible.

The rear facing side of the docking station 260 can include or attach to a connector assembly 275, 277 for attachment to a stand, mount, mounting arm 272, or the like. In one embodiment, the connector assembly can include a pin, hinge, swivel mechanism or the like for allowing rotation of the docking station 260 along a horizontal and/or vertical axis.

FIGS. 3A and 3B illustrate perspective views of an embodiment of a transport dock, carrier dock or transport cradle 300. In one embodiment, the transport dock 300 serves as a holder, cradle or a carrier for a handheld monitor 110. For example, the transport dock 300 can include an attachment mechanism to a bed frame, stand, ambulance interior, and or other mounting surface. In one embodiment, the transport dock 300 expands the capability of a handheld monitor 110 by, for example, providing docking ports for expansion modules 150. In some embodiments, the expansion modules 150 includes a display 305 on one side, where the display remains exposed even after the expansion module is docked.

In one embodiment, the transport dock 300 is roughly a rectangular box shape and can include one or more docking ports 310, 320 on one or more faces or on one or more sides. The docking ports 310, 320 can receive one or more expansion modules 150 and/or one or more handheld monitors 110. For example, the front of the transport dock can include a docking port 320 for receiving eclectically and/or mechanically the handheld monitor 110. A display can be part of the transport dock. Alternatively, the display can be part of the handheld monitor. In the illustrated embodiment, the body of the transport dock 300 includes two expansion docking ports 310 for two expansion modules 150. In the illustrated embodiment, the docking ports 310 are arranged behind the handheld dock 320 in order to more efficiently use space and reduce the length of the assembled transport dock. The transport dock 300 can further include an integrated handle 330 for enhancing the portability of the transport dock 300. In one embodiment, the transport dock 300 is attachable to a docking station 120, for example, via a docking port 130.

In the illustrated embodiment, the expansion module 150 is configured for ease of installation and removal from the transport dock 300. An extraction handle 332 can be provided on the exposed side of the expansion module when docked. The extraction handle can be made of rubber or other high friction material. Raised textures can be formed on the surface of the extraction handle 332 to increase friction. In one embodiment, the extraction handle 332 is integrated into the expansion module and can include a cable port for receiving a cable connector 334. In another embodiment, the extraction handle 332 is part of the cable connector 334 and attaches to the expansion module 150 through a locking mechanism, such as a tab, latch or pin system. In one embodiment, the locking mechanism to the expansion module 150 can be articulated by pushing the cable connector 334 into the extraction handle 332 or by otherwise moving the connector relative to the handle. In some embodiments, a docking port 336 on the expansion module can be generally linearly aligned with an extraction handle 332 to allow the expansion module 150 to be pulled out of the transport dock 300 by applying an outward linear force on the extraction handle 332. The transport dock 300 can include a locking mechanism 338 that may need to be released before removing the expansion module 150.

The transport dock 300 can provide additional portability and/or functionality to a handheld monitor 110. For example, the transport dock 300 can increase the parameter monitoring capability of the handheld monitor 110 by providing an interface and/or data connection with the one or more expansion modules 150. In one embodiment, the expansion modules 150 for attachment to the transport dock 300 and connection to the monitor 110 can be selected based on the intended use. For example, a transport dock 300 for use with a patient with head trauma can include a EEG module while a transport dock 300 for use with a heart patient can include a cardiac output module. In one embodiment, the transport dock module 300 can provide an additional power source to the handheld monitor 110.

Figure 3C:
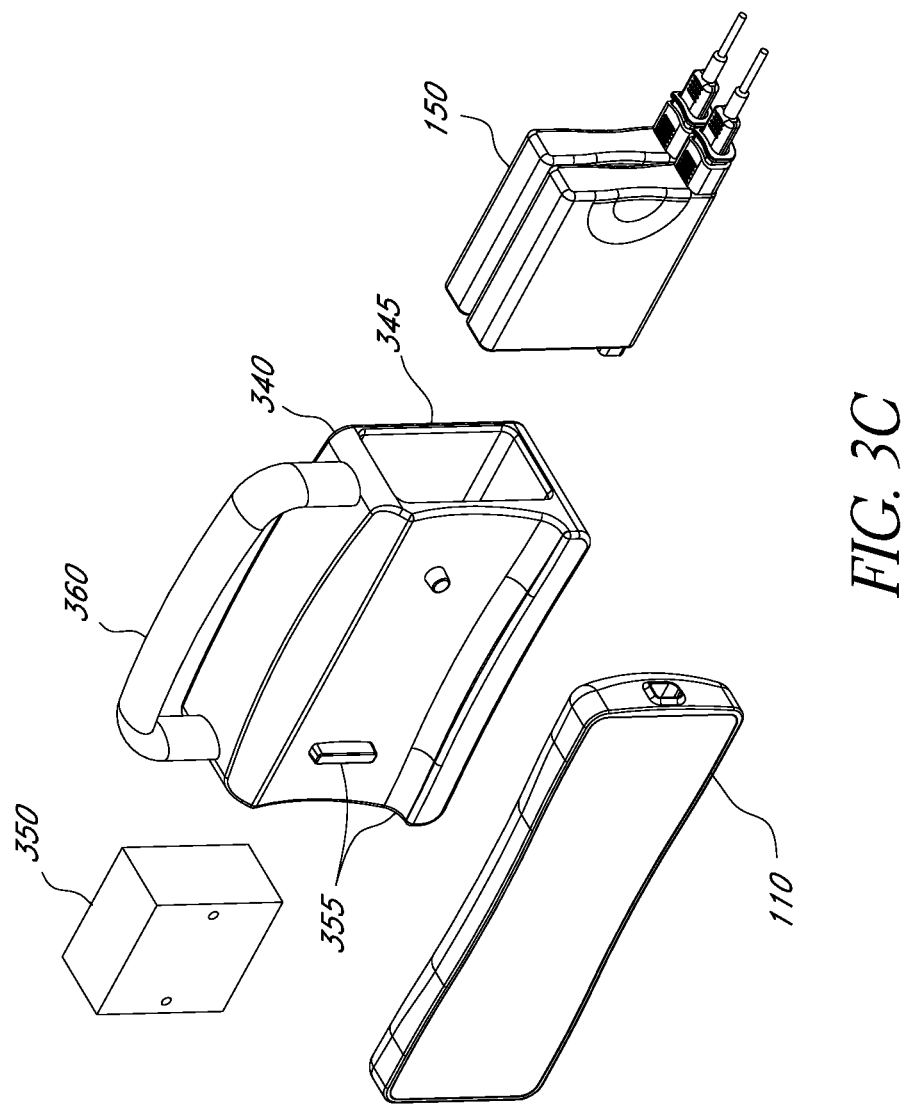
FIG. 3C illustrates a perspective view of another embodiment of a transport dock.

FIG. 3C illustrates a perspective view of another embodiment of a transport dock 340. The transport dock 340 includes a multi-module docking port 345 within the body, with an opening on one edge of the body for receiving multiple expansion modules 150. In one embodiment, the transport dock 340 includes another multi-module docking port 345 or other docking port for another monitoring component 350. For example, the monitoring component 350 can be a power source, such as a battery, for providing power during portable operation of the handheld monitor. The transport dock 340 includes docking port 355 for a mechanically and/or electrically receiving the handheld monitor 110 and a handle 360.

Figure 3D:
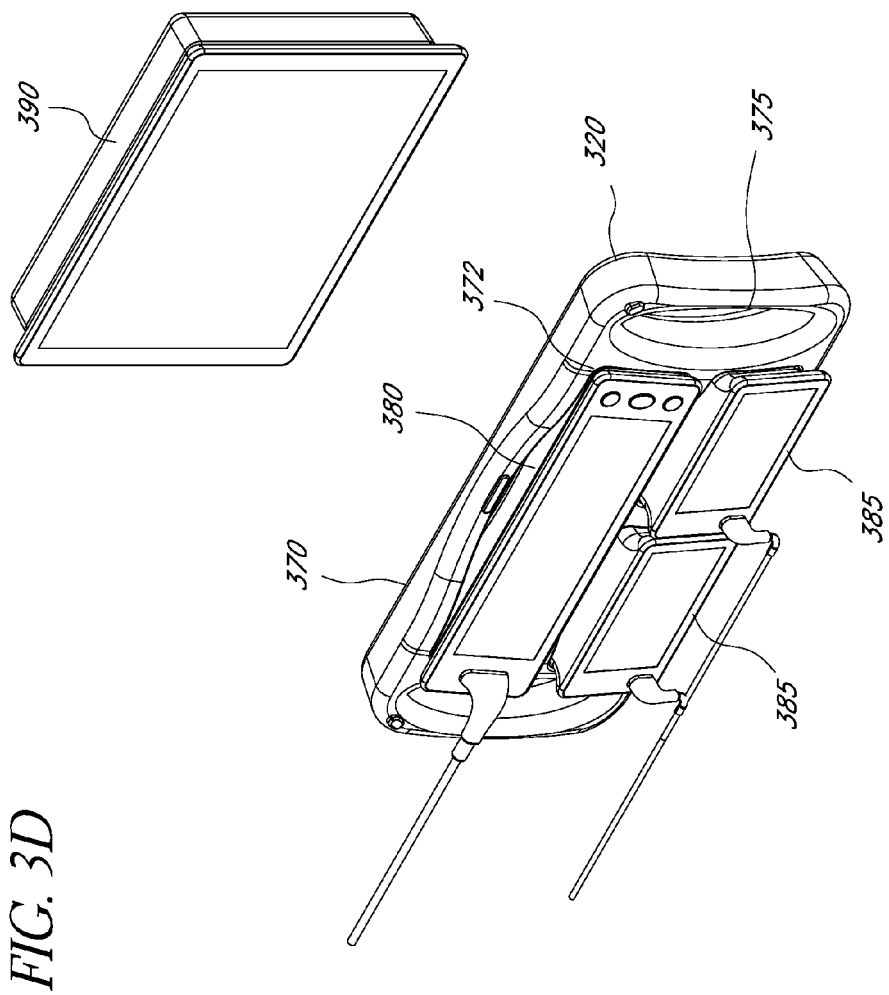
FIG. 3D illustrates a perspective views of another embodiment of a transport dock with a multi-size docking port.

FIG. 3D illustrates a perspective view of another embodiment of a transport dock 370 with a multi-size docking port 372. In the illustrated embodiment, the transport dock is roughly rectangular shaped with handles 375 on opposite edges. On the front of the transport dock 370 is a multi-sized docking port 372 for different sized handheld monitors 380, 385, 390. In one configuration, the docking port 372 can fit four small handheld monitors 385. In another configuration, the docking port 372 can fit two medium handheld monitors 380. In another configuration, the docking port 372 can fit one large monitor 390. In another configuration, the docking port 372 can fit a combination of small 385, medium 385, and/or large handheld monitors 390. As will be apparent, the docking port 372 can be configured to receive different combinations and numbers of handheld monitors.

In one embodiment, the transport dock 370 can include multiple docking ports in addition to or instead of a multi-size docking port 372. For example, the transport dock 370 can include to one medium sized docking port and two small sized ports. As will be apparent, different combinations and numbers of port sizes may be used.

Figure 3E:
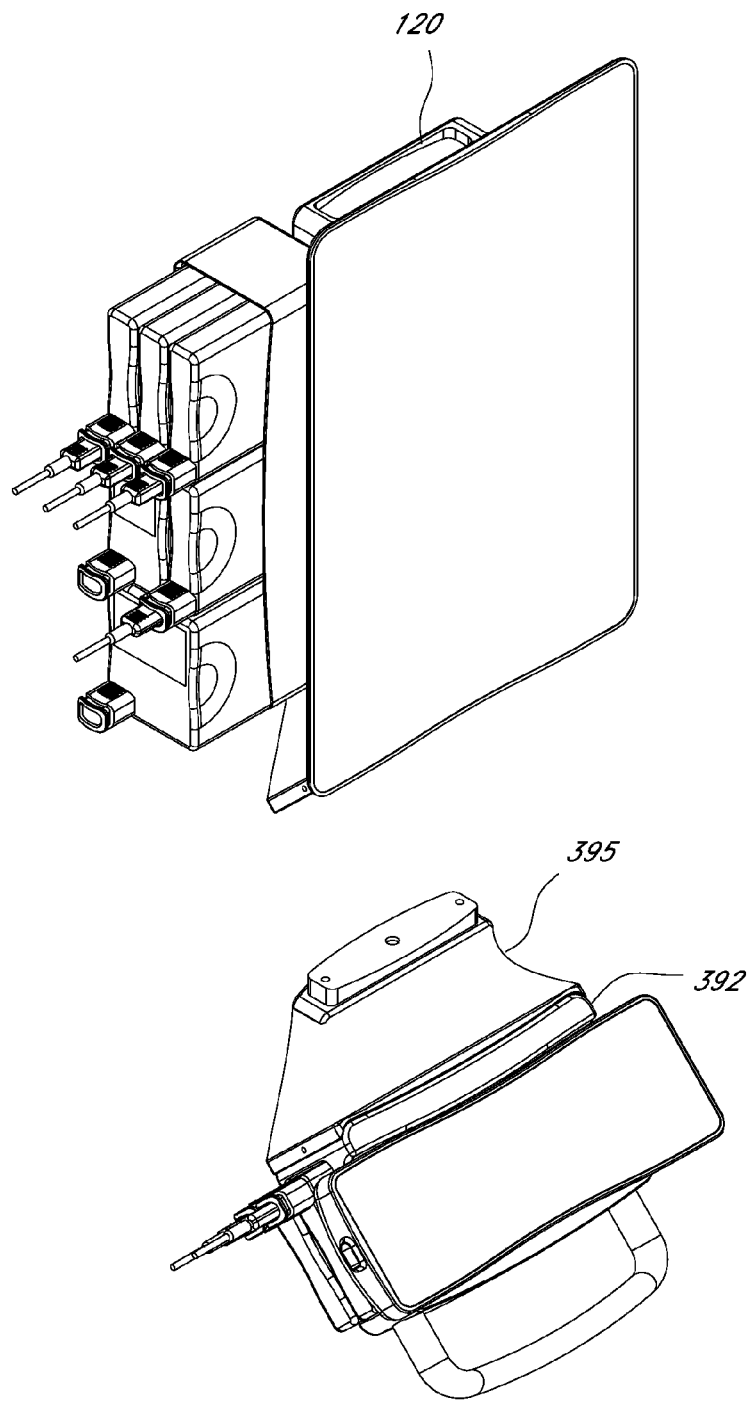
FIG. 3E illustrates a perspective views of another embodiment of a transport dock with an attached docking arm.

FIG. 3E illustrates a perspective views of another embodiment of a transport dock 392 with an attached docking arm 395. The docking arm 395 can be integrated or detachable from the transport dock. The docking arm 395 can be used to attach the transport dock 392 electrically and/or mechanically to a docking station 120.

FIGS. 4A-4F illustrate embodiments of a monitoring tablet. In some embodiments, the monitoring tablet is a transport dock with an integrated patient monitor.

Figure 4A:
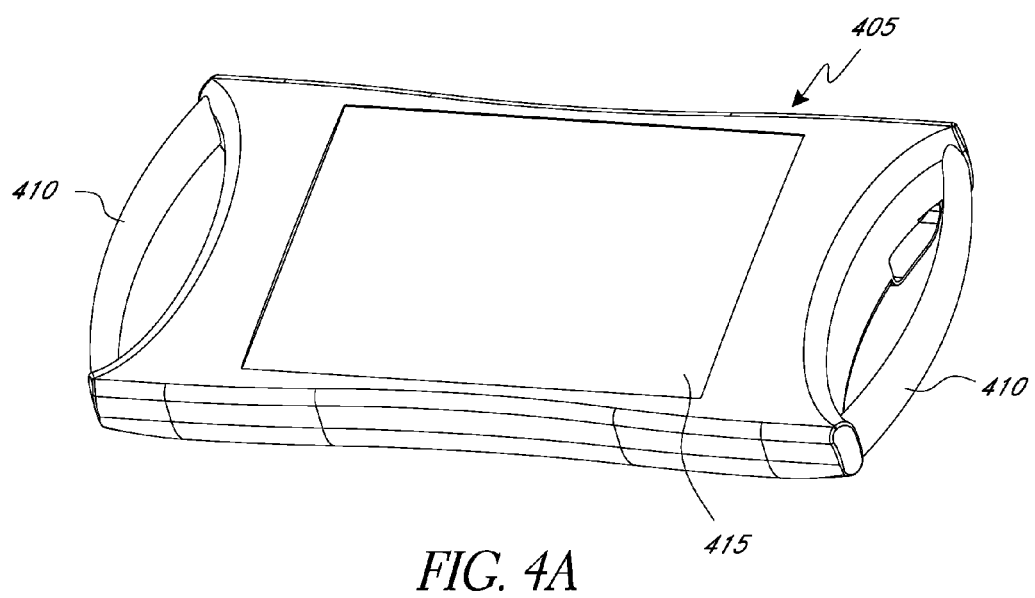
FIGS. 4A-4D illustrate embodiments of a monitoring tablet.

In FIG. 4A, the tablet 405 is roughly rectangular shaped with handles 410 on opposite edges. The display 415 displays one or more parameter values and/or waveforms of monitored parameters. The tablet 405 can have one or more controls, such as buttons, dials, or a touch screen. The tablet 405 can include a wireless transmitter and/or receiver for communicating with a physiological sensor, patient monitor and/or docking station.

Figure 4B:
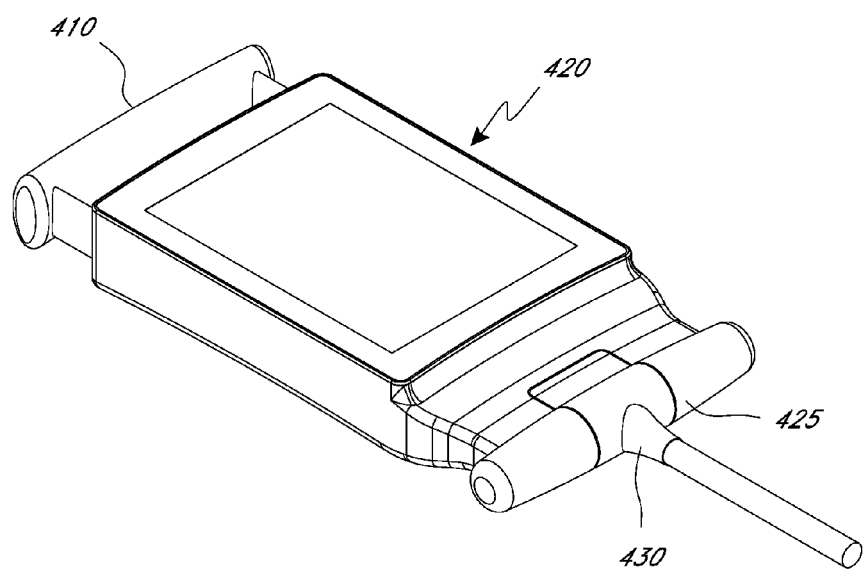

FIG. 4B illustrates a monitoring tablet 420 with a handle 410 on one edge and a docking port 425 for receiving a cable assembly 430 from a physiological sensor, docking station and/or patient monitor. As will be apparent, the handle 410 and docking port 425 can be located on any side of the monitoring tablet 420.

Figure 4C:
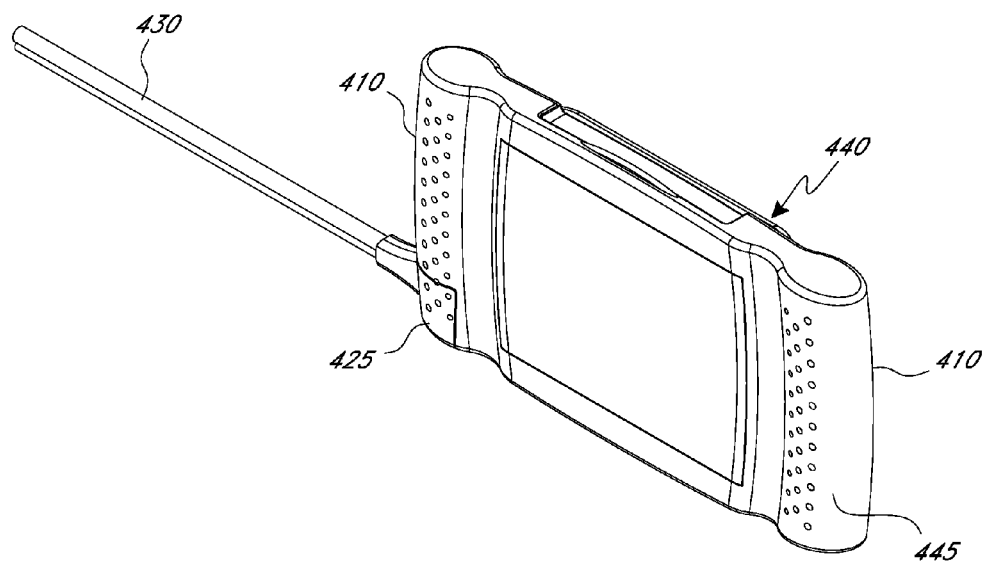

FIG. 4C illustrates another embodiment of a monitoring tablet 440. The monitoring tablet 440 includes handles along two, opposite sides 410. The handles 410 include a textured area 445, comprising bumps, protrusions, a mesh or web, or the like, for providing better grip for a user. In one embodiment, the textured area 445 comprises a rubberized grip. The handle 410 can include a docking port 425 for receiving a cable assembly 430.

Figure 4D:
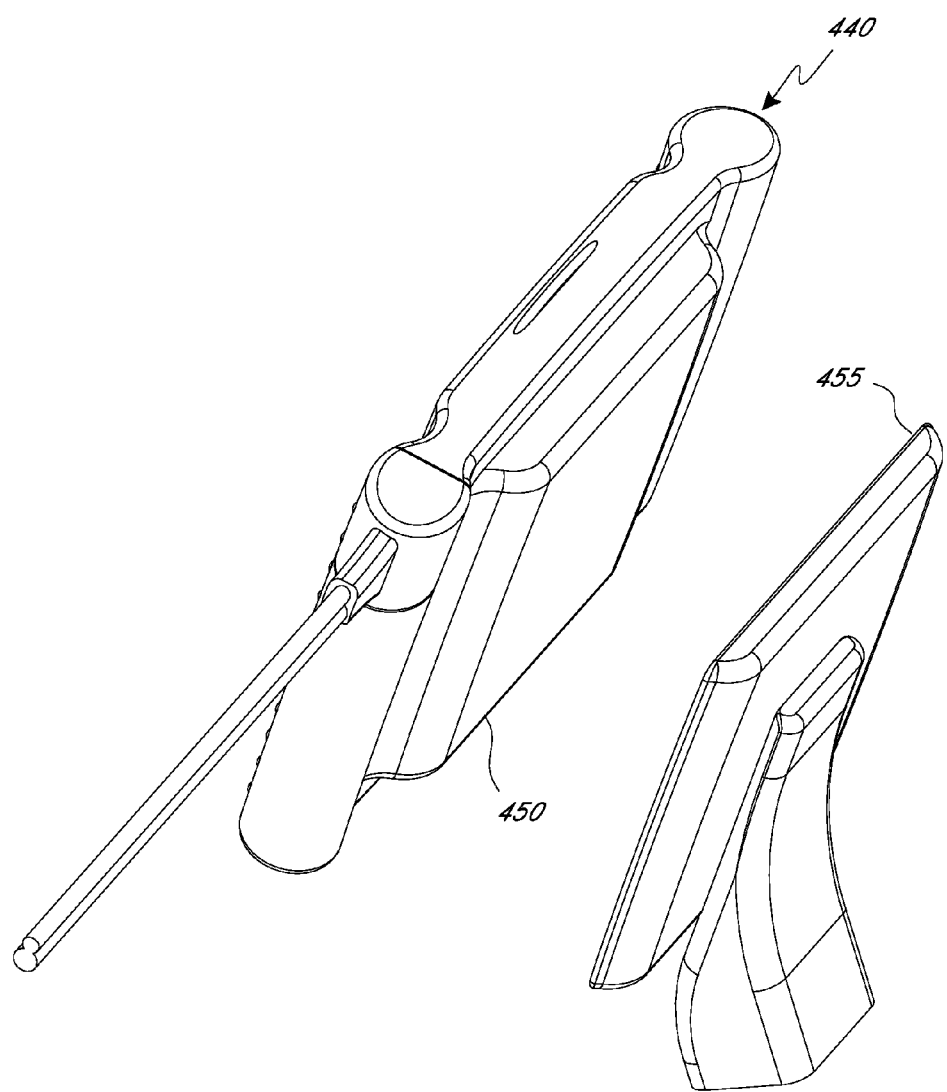

FIG. 4D illustrates an embodiment of the monitoring tablet 440 of FIG. 4C with a mounting surface 450 on the back for mounting the tablet 440 to a stand 455, mounting arm, or other mounting surface. In one embodiment, the monitoring tablet 440 attaches to a docking port 135 of a docking station 120. In one embodiment, the mounting surface 450 comprises input, output (I/O) and/or power connections, for example, for docking with a docking station.

Figure 4E:
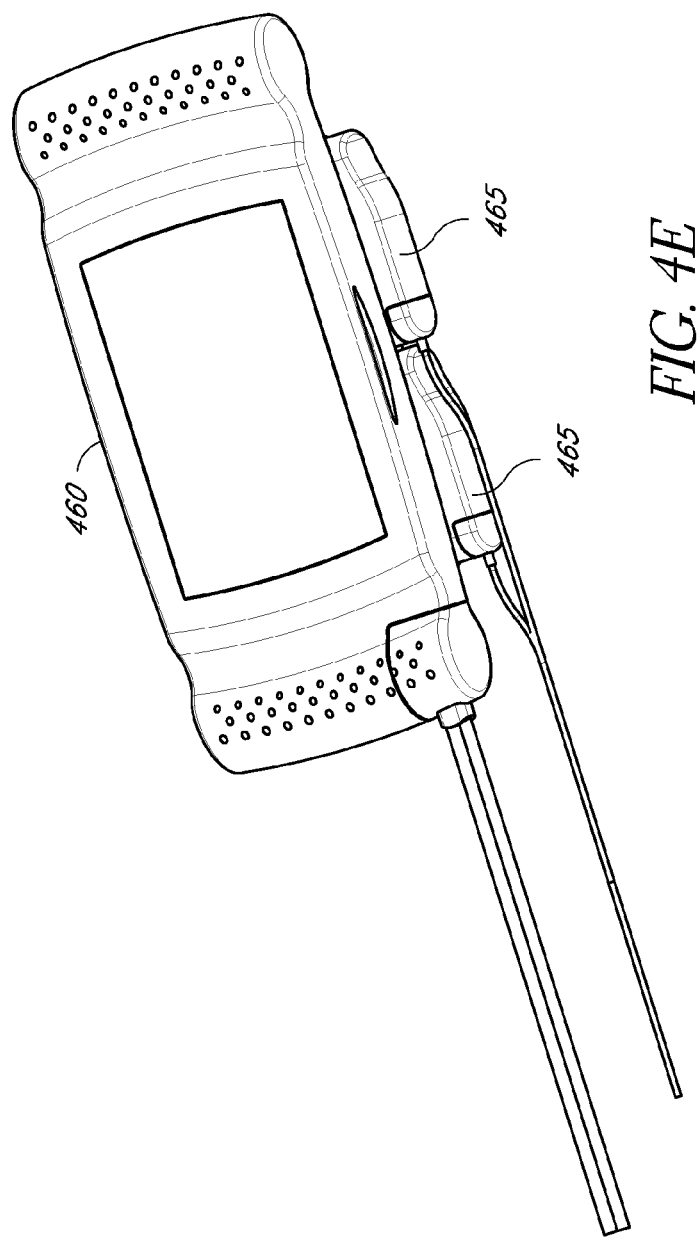

FIGS. 4E-4F illustrate perspective and exploded views, respectively, of a monitoring tablet embodiment 460 having multiple expansion slots for expansion modules 465. In one embodiment, the parameters or screen image that would ordinarily be displayed on the module displays when undocked are available for viewing in a window, tab, or the like on the monitoring tablet display. For example, there could be a tab on the tablet display that, when touched, causes the parameters or screen image from a module to appear.

Figure 1C:
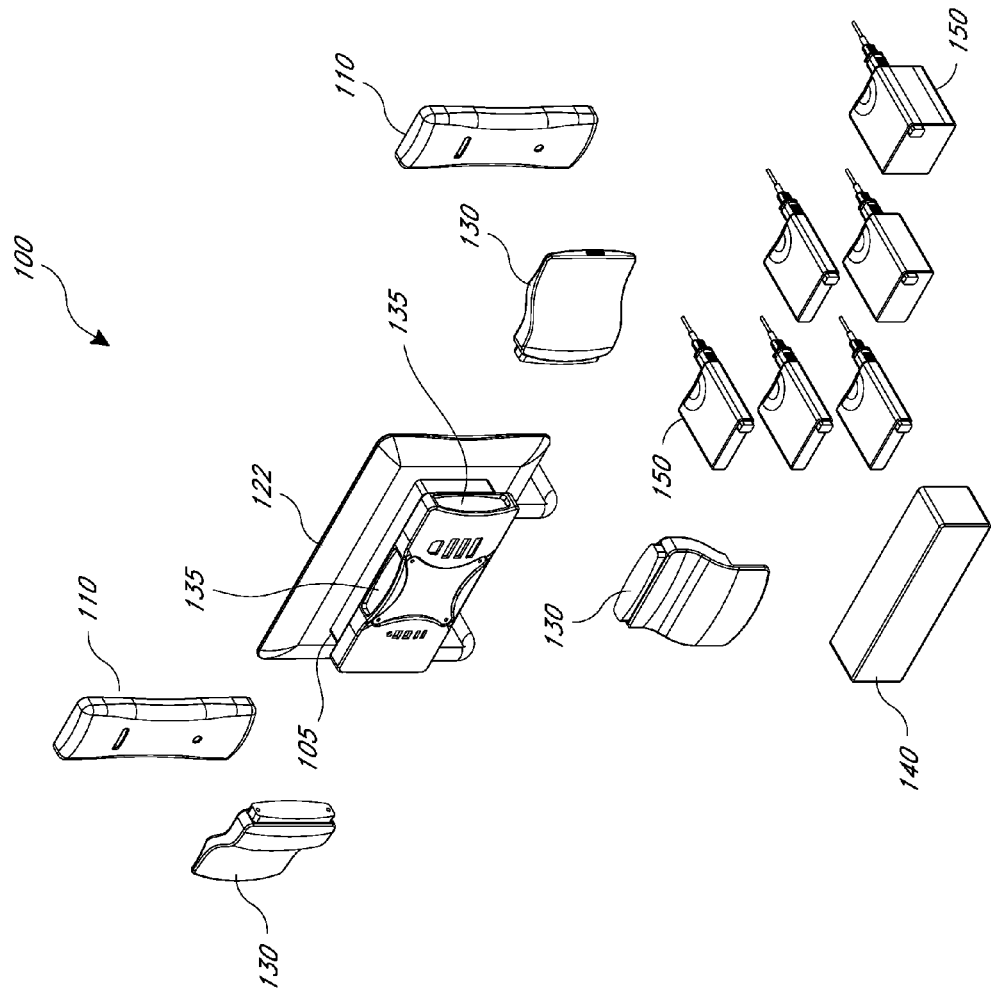

FIGS. 5A1-5D illustrate various docking station embodiments capable of receiving a transport dock, monitoring tablet, and/or handheld monitor. FIG. 5A1 illustrates the transport dock 370 of FIG. 3D attachable mechanically and/or electrically to a docking station 505 embodiment via a docking port 510. FIG. 5A2 illustrates an exploded view of the embodiment in FIG. 5A1.

Figure 5B:
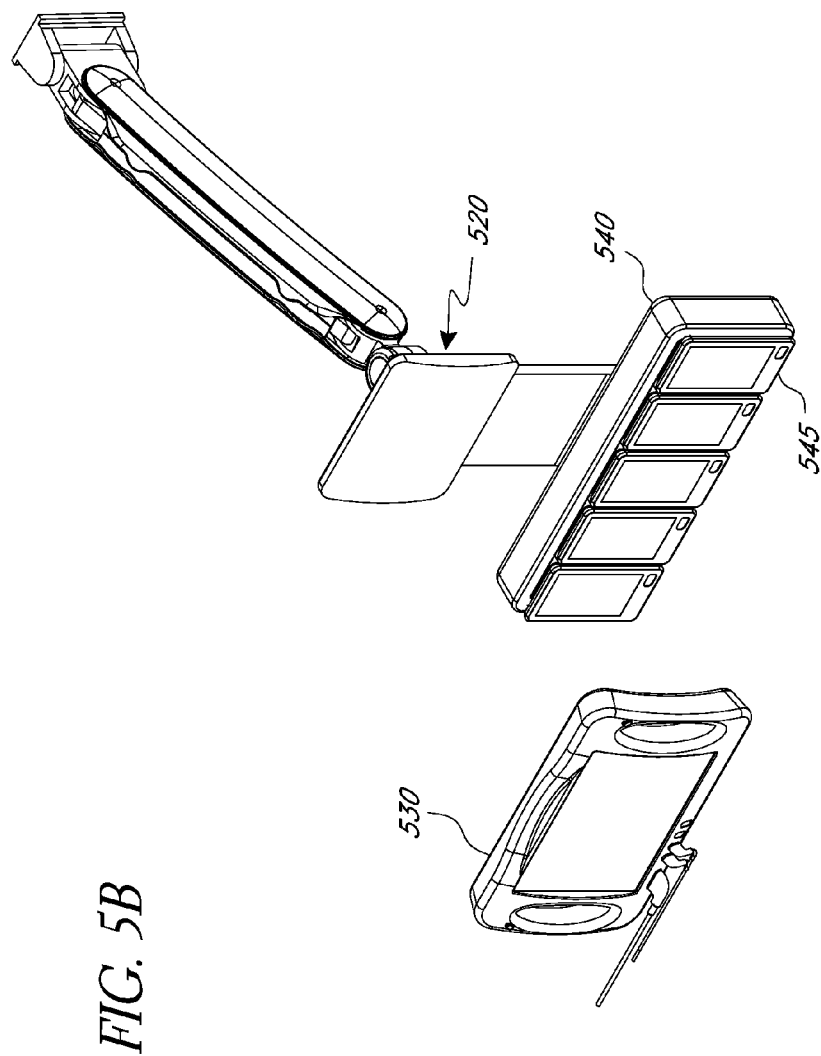

FIG. 5B illustrates a docking station embodiment 520 having docking ports for a monitoring tablet 530 and a transport dock 540. In one embodiment, the docking station 520 does not include an integrated patient monitor or display. The transport dock 540 can include multiple docking ports for receiving multiple portable monitors 545. The portable monitors 545 can be expansion modules with displays to increase the available display space. For example, additional portable monitors 545 can be added in order to measure and/or monitor additional parameters. In the illustrated embodiment, the docking station 520 is attached to a mounting arm.

Figure 5C:
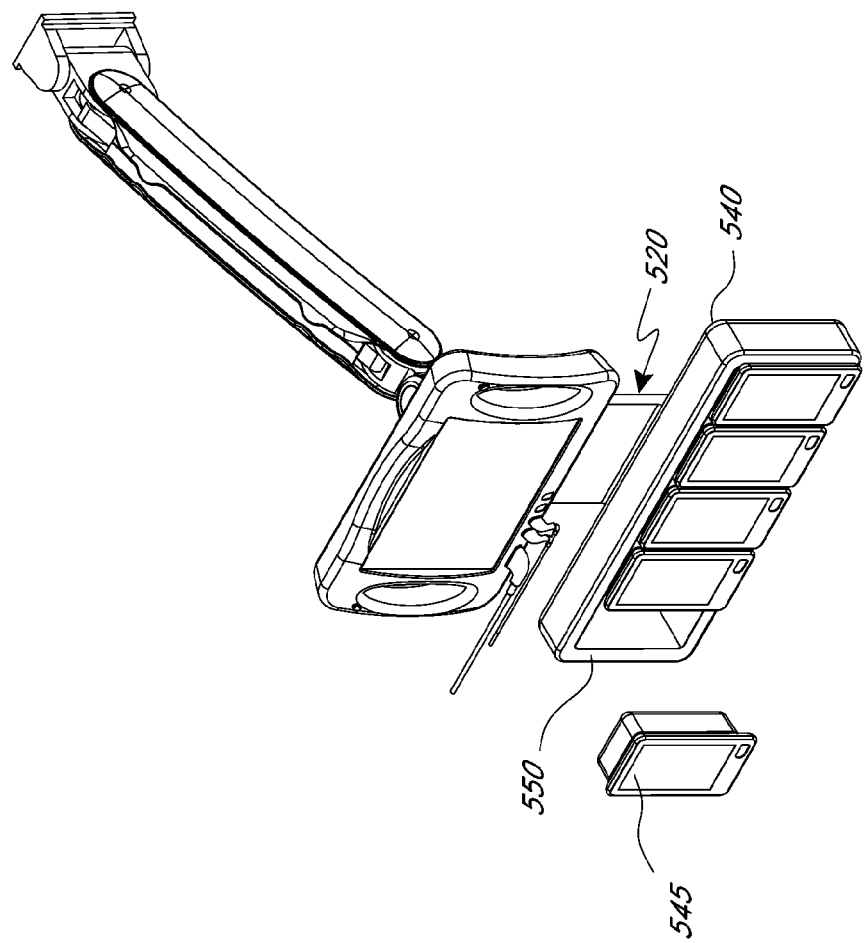

FIG. 5C illustrates the transport dock 540 of FIG. 5B with a portable monitor 545 removed from its docking port 550.

Figure 5D:
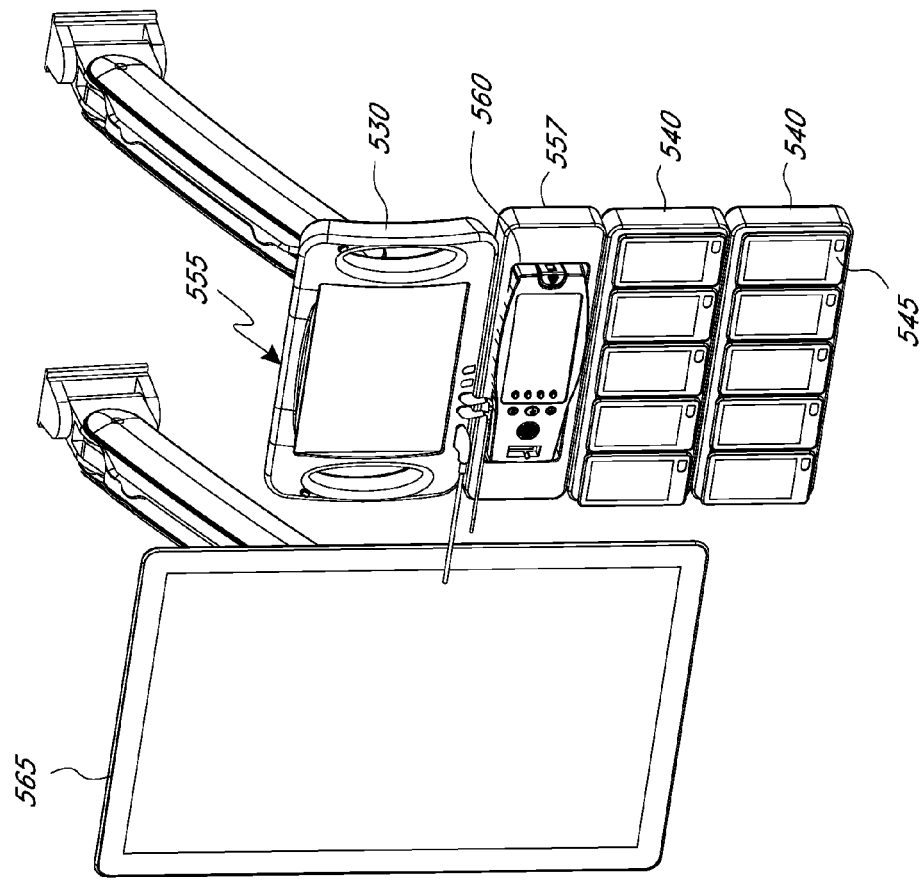
Figure 5E:
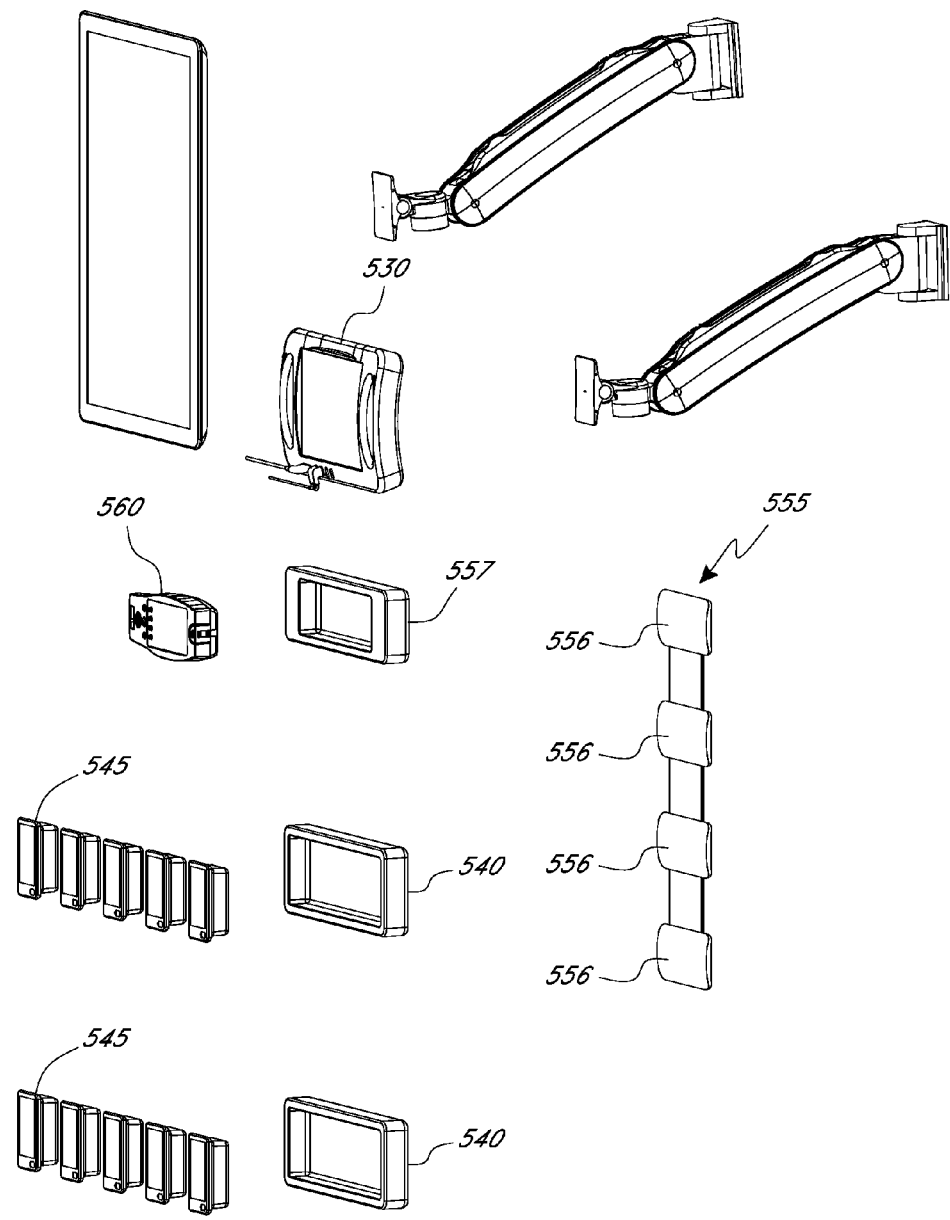

FIG. 5D illustrates a docking station embodiment 555 with docking ports for multiple transport dock 540, 557, multiple types of transport docks, and/or one or more monitoring tablets 530. FIG. 5E illustrates an exploded view of the docking station embodiment 555. In one embodiment, the transport docks 540, 557 can provide docking ports 556 for multiple types of handheld monitors 545, 560. In one embodiment, the handheld 560 is a Radical® or Radical-7™ handheld monitor.

In one embodiment, the docking station 555 operates in tandem or in communication with a patient monitor 565 or another docking station. The docking station 555 can communicate with the patient monitor 555 through a wired or wireless communications medium.

FIG. 6 illustrates a front view of the embodiment of the modular patient monitor 600 of FIGS. 2H-2J, displaying measurements for parameters across multiple displays. The multiple displays can be part of one or more components of the modular patient monitor 600, such as a first display 601 (e.g. primary or integrated display), one or more portable monitors 602, 603, and/or one or more expansion modules 605. Measurements can be spanned across the multiple displays, for example, by displaying a partial set of the measurements on the first display 601 and additional measurements on a portable monitor 602, 603. In one embodiment, instant readings, such as current numerical measurements 625, 630, can be displayed on one display (e.g. on the portable monitor display 625, 630) while measurements over time, such as waveforms 609, 615, 617 are displayed on another display (e.g. on the first display 601 or on an expansion module 605). Thus, a user can refer to one display for a summary of a status of a monitored patient, while referring to another display for more detailed information. Images 610 derived from the patient, such as ultrasound images, thermal images, optical coherence tomography (OCT) images can also be displayed on one or more displays.

In one embodiment, measurements of the parameters can be organized into different views that are shown on the displays of the patient monitor 600. For example, views can include a standard format, a tend-centric logically grouped format, or an expandable view where measurement screens are collapsed into a diagram or representation (e.g. the human body, brain, lungs, peripheries, or the like) that can be viewed in more detail by selecting sections of the diagram.

In one embodiment, one portable monitor 602 can be for a one part of the body, such as the head, measuring parameters for that particular part, (e.g., cerebral oximeter, EEG, core pulse CO-oximetry, pulse oximetry of the forehead, ear, or carotid, or the like) while another potable monitor 603 is for another part of the body, such as the periphery and lungs, and measuring parameters for that second part (e.g., pulse CO-Oximetry or pulse oximetry of the periphery or digit, RAM, ECG, blood pressure, organ, liver or kidney oximetry, or the like).

Measurements on the display or other portions of the display can be highlighted, colored, flashed, or otherwise visually distinguished in order to alert or notify users of important or irregular measurements. For example, normal measurements can be displayed in green, abnormal in yellow and critical measurements in red. As discussed above, measurements can be displayed for many different parameters, such as EEG, BP, ECG, temperature, cardiac output, oxygen saturation ($SpO_2$), pulse rate (PR), perfusion index (PI), signal quality (SiQ), a pulse waveform (pleth), as well as other parameters.

In some embodiments, a user can select which measurements to display, drop, and/or span using controls 620 on the modular patient monitor 600. The controls 620 can be physical controls (e.g. buttons, switches) or virtual controls (e.g. touch screen buttons). In some embodiments, the monitor 600 can have an algorithm for selecting measurements to display, drop, and/or span, such as by ranking of measurements, by display templates or by user preferences. In some embodiments, the controls can alter, initiate, suspend or otherwise change the procedures being performed on the patient. For example, an anesthesiologist may increase the level of anesthesia provided to the patient or a doctor can begin therapy treatment by inputting commands through the controls. In one embodiment, the patient monitor 600 may request identification (e.g. login, password, ID badge, biometrics, or the like) before making any changes.

Figure 7:
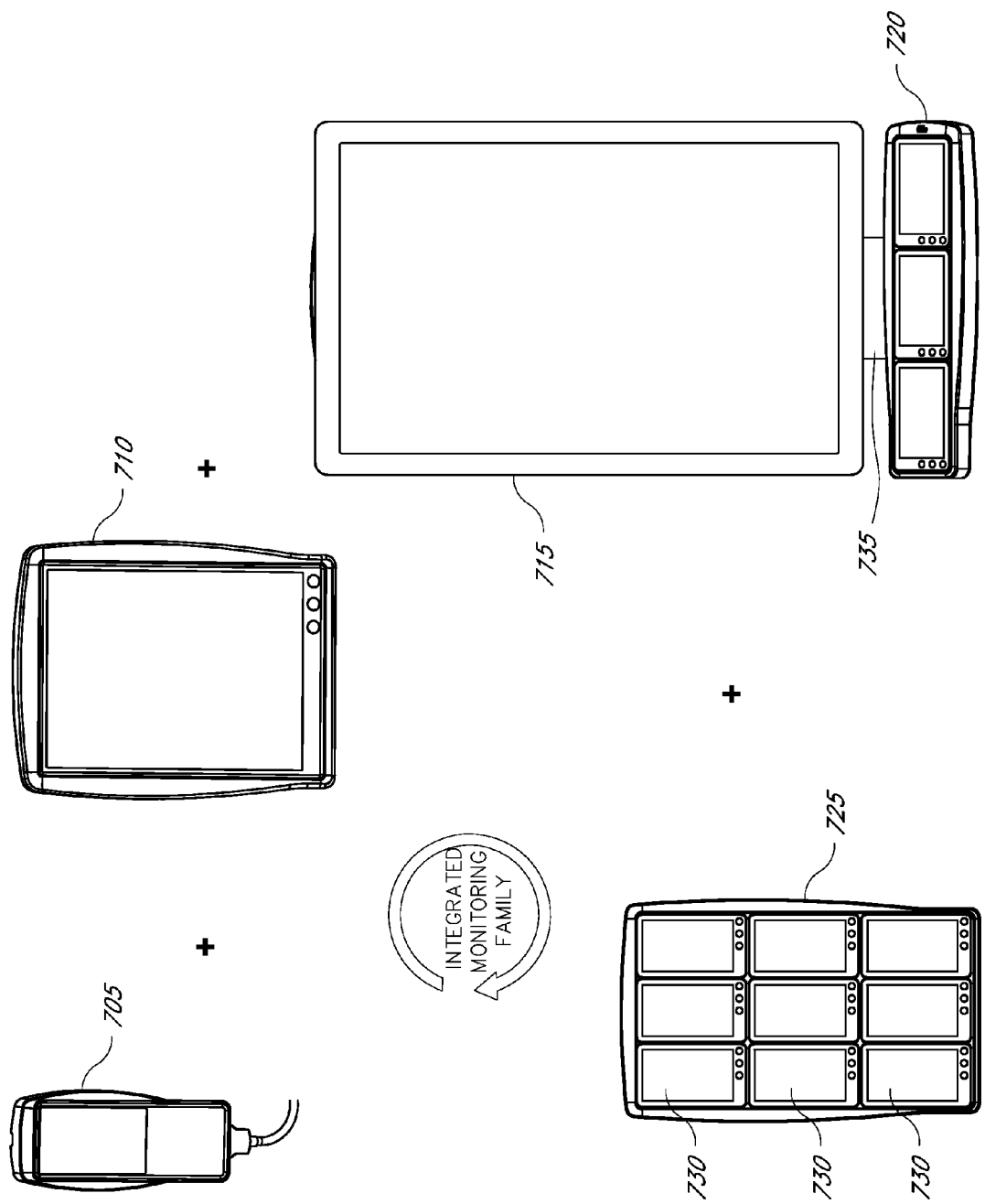
FIG. 7 illustrates a general block diagram of a physiological monitoring family.
Figure 8E:
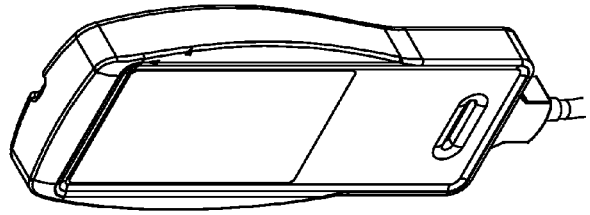
FIGS. 8A-E are top, front, bottom, side and perspective views, respectively, of a handheld monitor embodiment.
Figure 8D:
Figure 8A:
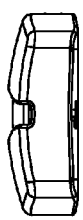
Figure 8B:
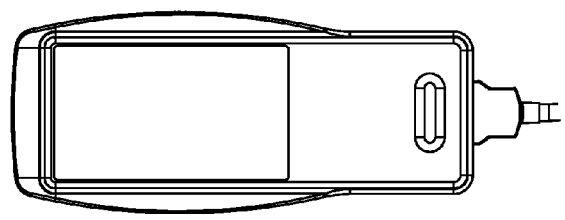
Figure 8C:
Figure 9D:
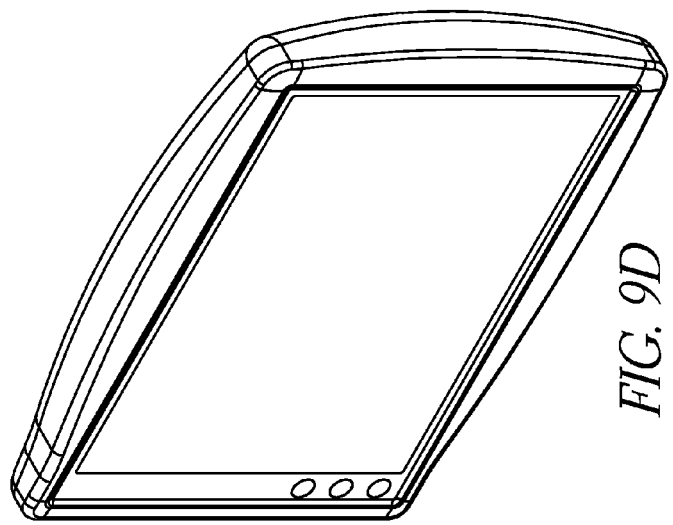
FIGS. 9A-D are top, front, side and perspective views, respectively, of a tablet monitor embodiment.
Figure 9C:
Figure 9A:
Figure 9B:
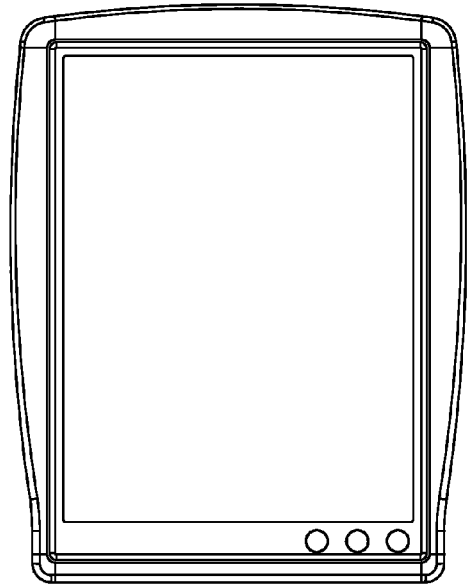
Figure 10E:
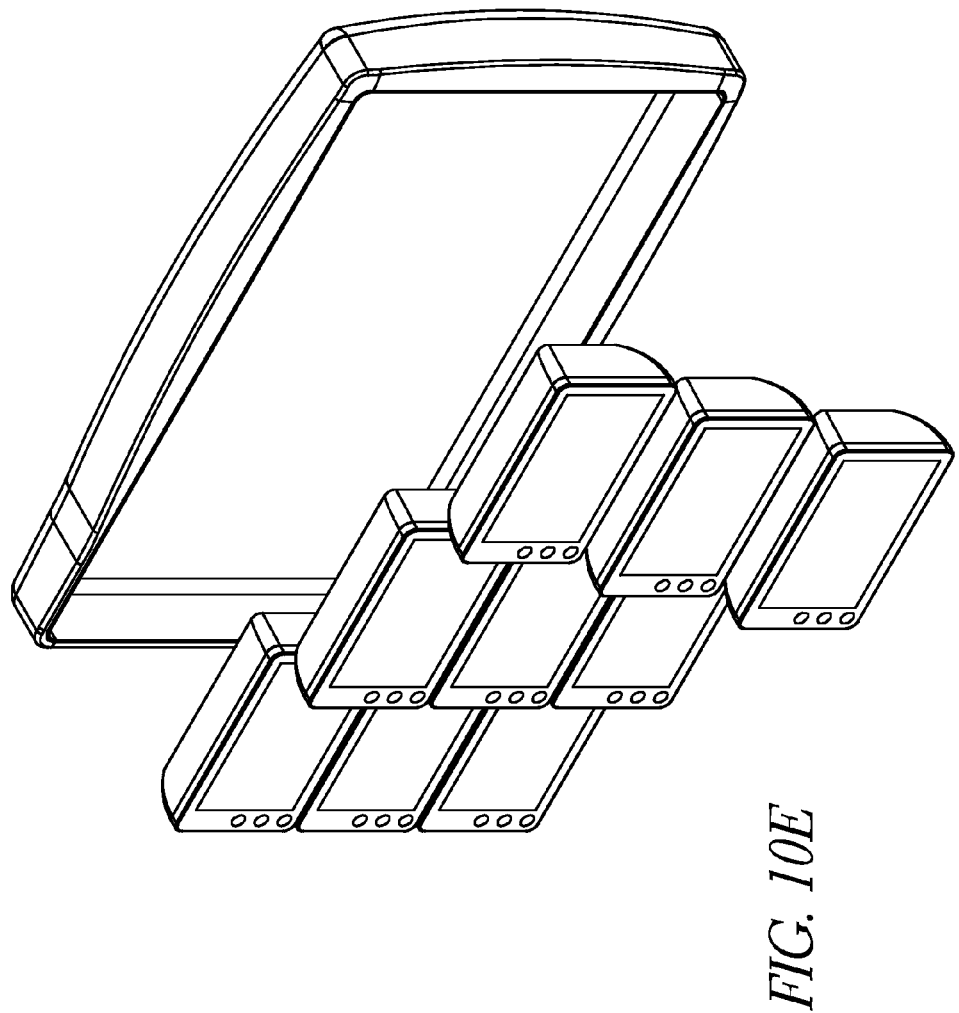
Figure 11B:
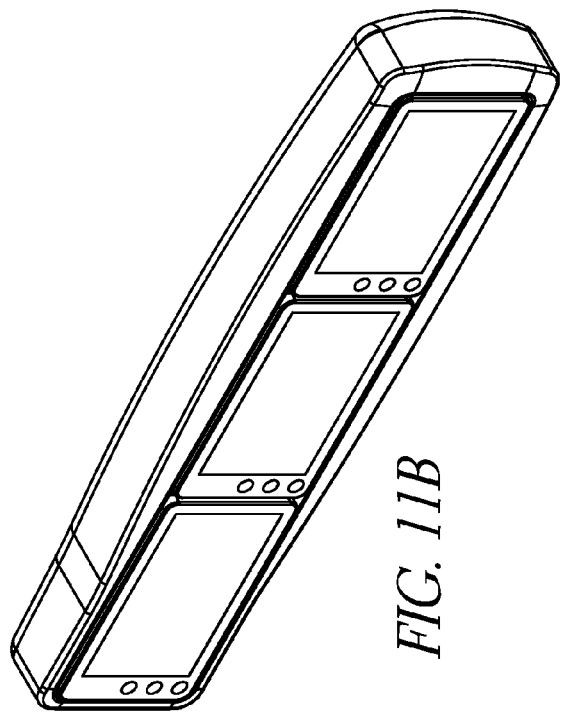
FIGS. 11A-E are top perspective, front, side, and exploded views, respectively, of a 1×3 rack embodiment with mounted monitor, control and/or display modules.
Figure 11D:
Figure 11A:
Figure 11C:
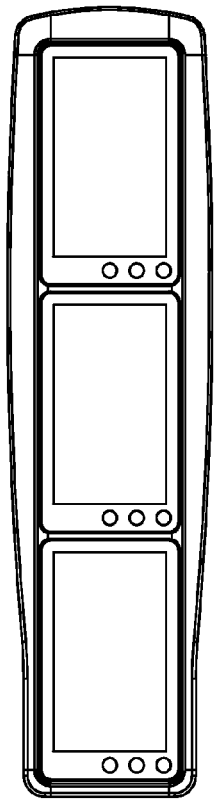
Figure 11E:
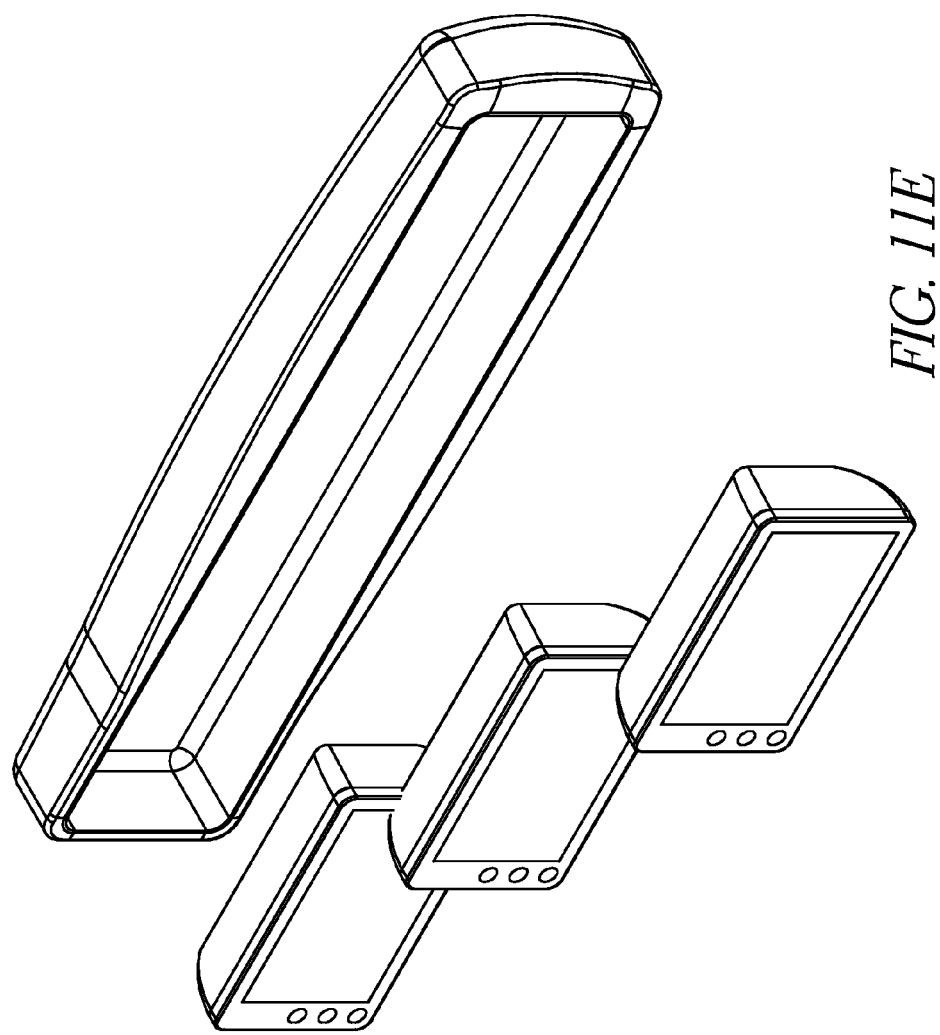

FIG. 7 illustrates a general block diagram of an embodiment of a physiological monitoring family. FIG. 7 illustrates a physiological monitoring family 700 having a handheld monitor 705, a tablet monitor 710, a full-sized display 715, a 1×3 module rack or dock 720, a 9×9 module rack or dock 725, and corresponding monitor modules 730 (e.g. expansion module or handheld monitor). In some embodiments, one or more components can function, alone or in combination, as a patient monitor. In an embodiment, the monitoring family 700 can be in communication with a sensor array, which can include optical and acoustic sensors for measuring blood parameters, such as oxygen saturation; and acoustic parameters, such as respiration rate; and for body sound monitoring. In an embodiment, sensor data is transmitted via cables or wirelessly to the monitors or to local or wide area hospital or medical networks.

In one embodiment, the large display 715 integrates data from a tablet 710, hand held 705 or various module monitors 730. In one embodiment, the large display includes a patient monitor and provides a platform for an enhanced situational awareness GUI. A display bracket 735 allows removable attachment of various devices, including a 1×3 rack 720 or a tablet monitor 710, to name a few. The rack embodiment contains one or more removable OEM monitor, control or display modules 730. These embodiments can function as a multiple parameter monitor having flexible user interface and control features. In one embodiment, the tablet monitor 710 has a removable user interface portion for the monitor (e.g. remote control or other input device) and/or touch screen controls for the display.

FIGS. 8A-E are top, front, bottom, side and perspective views, respectively, of the handheld monitor embodiment 705 of FIG. 7.

FIGS. 9A-D are top, front, side and perspective views, respectively, of the tablet monitor embodiment 710 of FIG. 7.

FIGS. 10A-E are top, front, side, perspective and exploded views, respectively, of the 3×3 rack embodiment 725 of FIG. 7 with mounted display modules. In one embodiment, the mounted display modules are multiple single parameter monitor modules. In an embodiment, each removable module has a wired or wireless network connection (e.g., 802.11, BLUETOOTH or the like), a 4.3" display and a battery for standalone operation. This allows each module to be used as a single parameter transport monitor, as well as used as part of a larger modular patient monitoring system. In some embodiments, the module mechanical form and fit and the electrical/electronic interfaces are standardized to advantageously allow for the integration of OEM acute care monitoring, control and display technologies into the physiological monitoring family.

FIGS. 11A-E are top perspective, front, side, and exploded views, respectively, of a 1×3 rack embodiment 720 of FIG. 7 with mounted monitor, control and/or display modules.

FIGS. 12A-D are top, front, side and perspective views, respectively, of the large display 715 and display bracket 735 of FIG. 7.

Figure 13A:
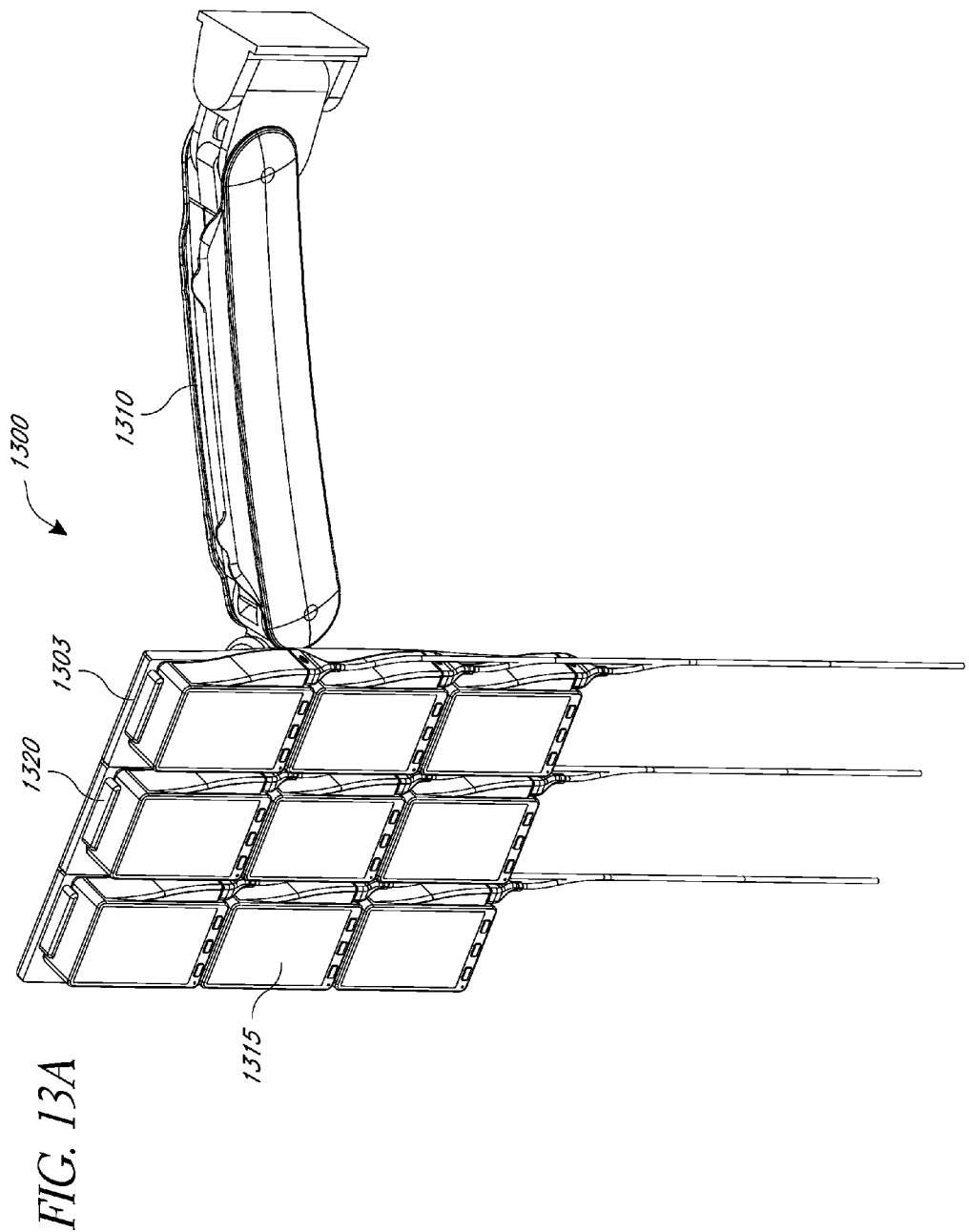
FIGS. 13A-B are perspective and exploded views of another embodiment of a modular patient monitor.
Figure 13B:
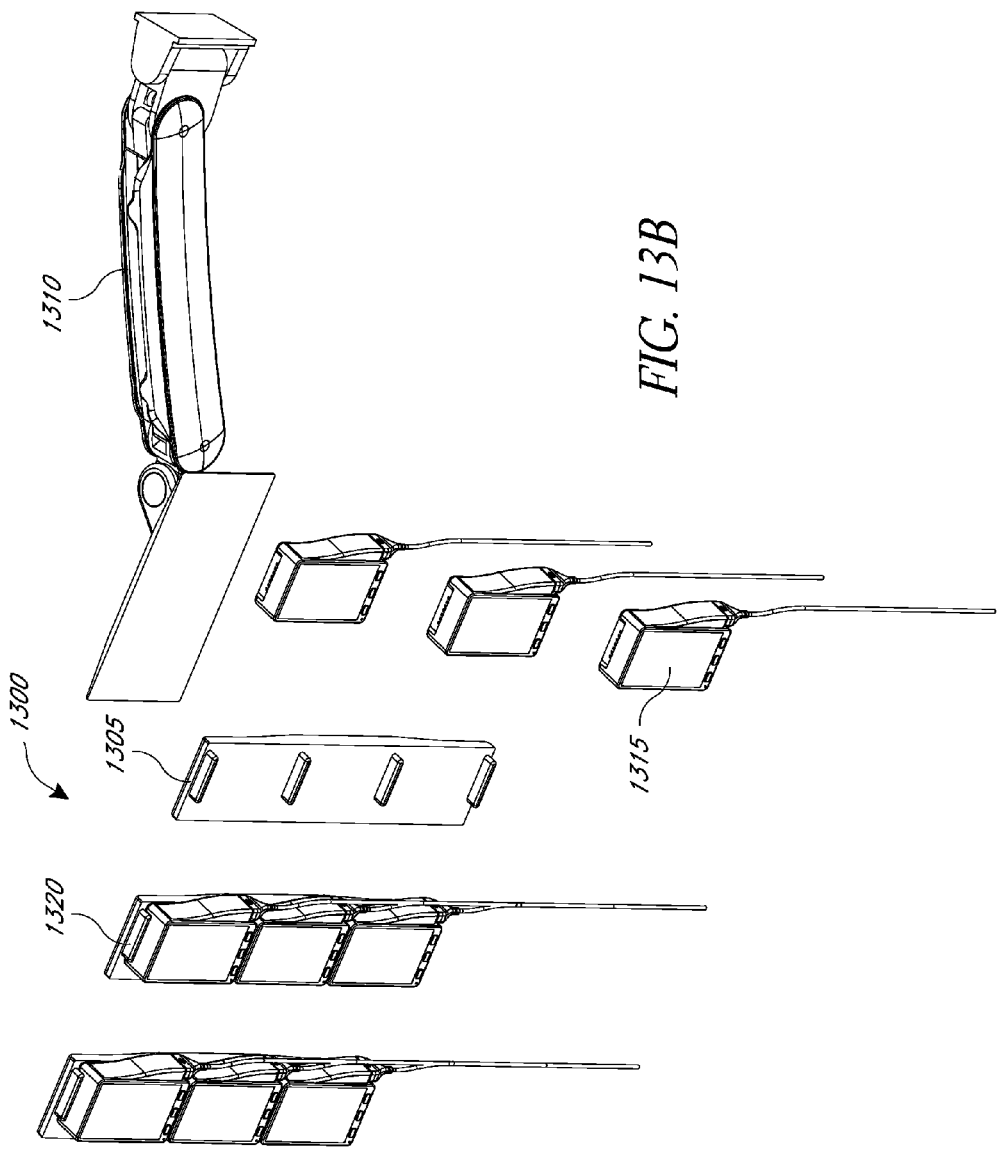

FIGS. 13A-B are perspective and exploded views of another embodiment of a modular patient monitor 1300. In the illustrated figure, a docking station 1303 is attached to a movable mount or arm 1310 on its back side, while its front side comprises multiple docking ports 1320 for multiple monitor modules 1315. The illustrated monitor module 1315 includes a cable port on the side that can provide improved cable management. For example, by having the port on the side, sensor cables that attach to the monitor can be kept from blocking the display. In one embodiment, the docking station 1303 can comprise a 3×3 rack with sufficient space between columns to allow cables to run between the columns. This can improve organization and cable management for the modular patient monitor 1300. In an embodiment, the docking station 1303 is comprised of multiple module racks (e.g. three 1×3 module racks) attached together.

Figure 13C:
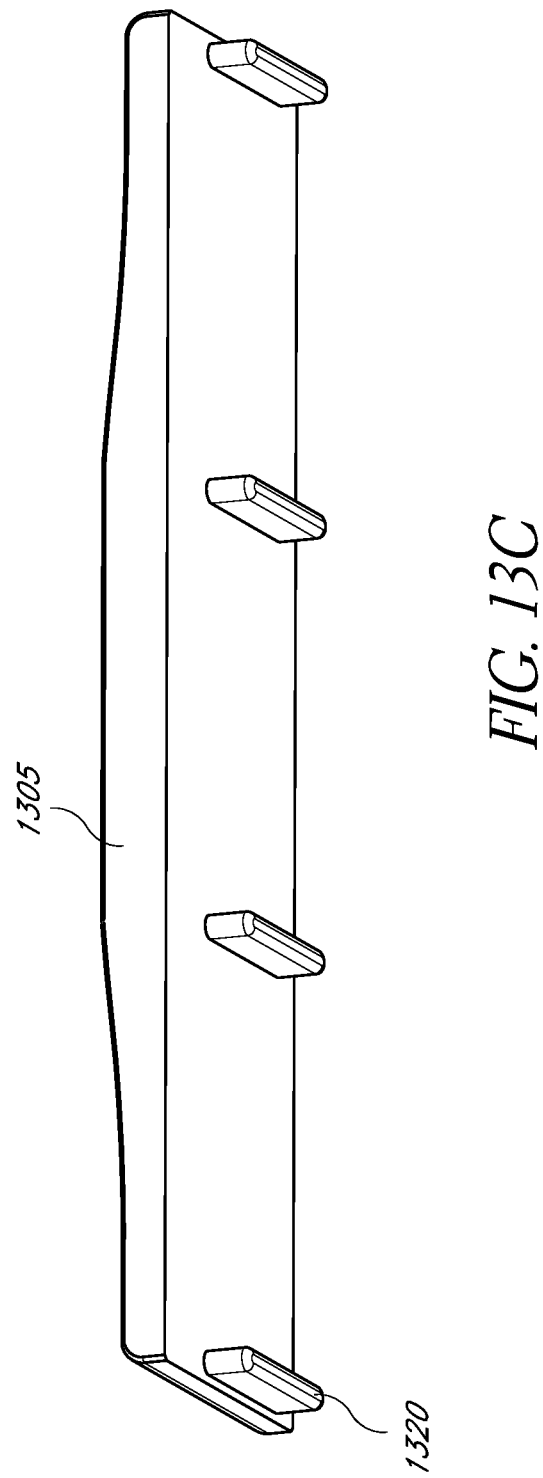
FIG. 13C illustrates a perspective view of an embodiment of a 3×1 docking station.

FIG. 13C illustrates a perspective view of an embodiment of a 1×3 module rack. The illustrated module rack 1305 includes raised supports 1320 for supporting and/or attaching to one or more of the edges (e.g. top and bottom) of a handheld monitor or expansion module. The supports 1320 can include connections for providing power and/or data communication to the handheld monitor or expansion module.

FIGS. 14A-B illustrates an embodiment of the monitor module 1315 of FIG. 13A-13B used in combination with a single port dock 1405. The dock 1405 can include a mounting point for a stand 1410. In one embodiment, the monitor module 1315 can be directly connected to the stand 1410 without using the dock 1405.

Figure 15:
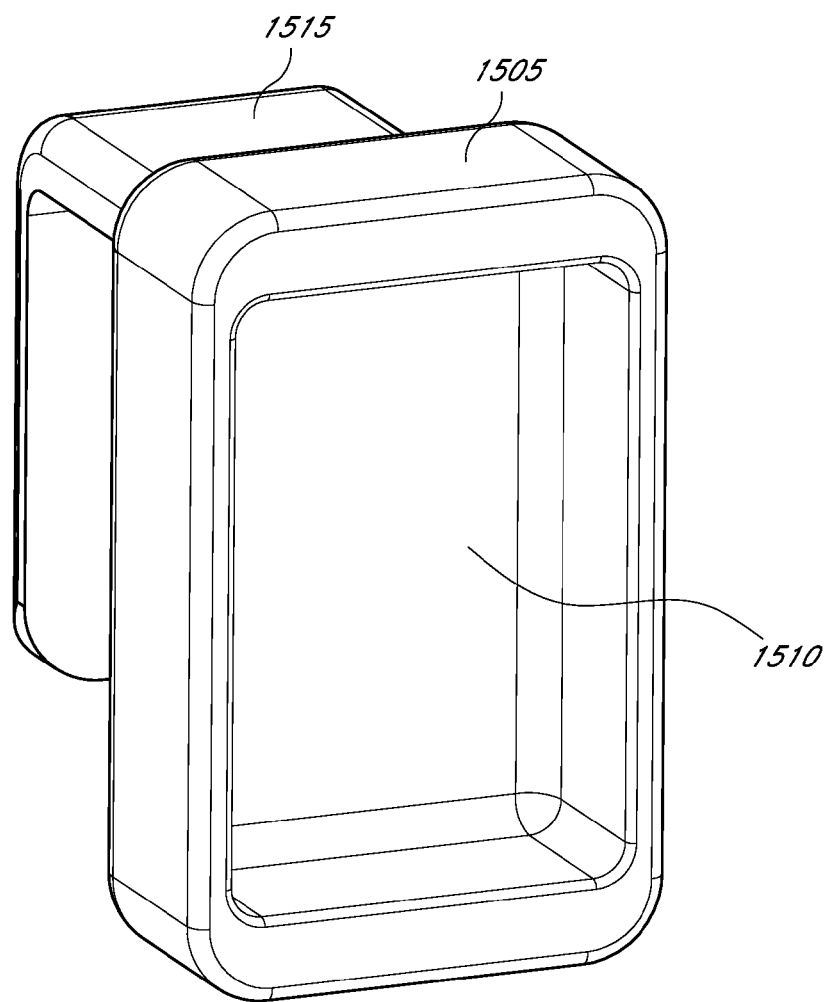
FIG. 15 illustrates an embodiment of a single port dock.

FIG. 15 illustrates an embodiment of a single port dock 1505. The dock can include a docking port 1510 for a module monitor and an attachment clip or hook 1515. The attachment clip 1515 can be used to attach the dock 1505 to a bed, stand, or other attachment point.

Modular patient monitors, transport docks, and docking stations have been disclosed in detail in connection with various embodiments. These embodiments are disclosed by way of examples only and are not to limit the scope of the claims that follow. One of ordinary skill in art will appreciate many variations and modifications. Indeed, the novel methods and systems described herein can be embodied in a variety of other forms; furthermore, various omissions, substitutions and changes in the form of the methods and systems described herein can be made without departing from the spirit of the inventions disclosed herein. The claims and their equivalents are intended to cover such forms or modifications as would fall within the scope and spirit of certain of the inventions disclosed herein.

One of ordinary skill in the art will appreciate the many variations, modifications and combinations possible. For example, the various embodiments of the patient monitoring system can be used with sensors that can measure any type of physiological parameter. In various embodiments, the displays used can be any type of display, such as LCDs, CRTs, plasma, and/or the like. Further, any number of handheld monitors and/or expansion modules can be used as part of the patient monitoring system. In some embodiments, the expansion modules can be used instead of handheld monitors and vice versa. Further, in some embodiments, parameters described above as measured by a monitor can be enabled by an expansion module and/or monitors can have built functionally to monitor parameters described as enabled by an expansion module. In some embodiments, the modular monitoring system 100 can use multiple types of docking ports to support various different monitoring components. Embodiments of the transport dock can support any number of handheld monitors and/or expansion modules, depending on the configuration of the dock.

In certain embodiments, the systems and methods described herein can advantageously be implemented using computer software, hardware, firmware, or any combination of software, hardware, and firmware. In one embodiment, the system includes a number of software modules that comprise computer executable code for performing the functions described herein. In certain embodiments, the computer-executable code is executed on one or more computers or processors. However, a skilled artisan will appreciate, in light of this disclosure, that any module that can be implemented using software can also be implemented using a different combination of hardware, software or firmware. For example, such a module can be implemented completely in hardware using a combination of integrated circuits. Alternatively or additionally, such a module can be implemented completely or partially using specialized computers or processors designed to perform the particular functions described herein rather than by general purpose computers or processors.

Moreover, certain embodiments of the disclosure are described with reference to methods, apparatus (systems) and computer program products that can be implemented by computer program instructions. These computer program instructions can be provided to a processor of a computer or patient monitor, special purpose computer, or other programmable data processing apparatus to produce a machine, such that the instructions, which execute via the processor of the computer or other programmable data processing apparatus, create means for implementing the acts specified herein to transform data from a first state to a second state.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

What is claimed is:

1. A docking station for a modular patient monitoring system, the docking station comprising:
 a first display screen;
 a plurality of docking ports integrated to a backside of the first display screen, the plurality of docking ports configured to receive monitoring components, the docking ports forming a mechanical and electrical connection with the monitoring components, the plurality of docking ports interchangeably usable by different monitoring components;
 a first removable docking arm which connects to at least one of the plurality of docking ports, the first docking arm configured to mechanically and electrically dock with a portable monitor, the docking arm configured to extend the docking port beyond the first display screen so that when the portable monitor is docked to the first docking arm the portable monitor is unobstructed by the first display screen, wherein the first docking arm is configurable to a variety of orientations; and
 a second docking port of the plurality of docking ports, the second docking port configured to receive at least an expansion module, the expansion module forming a mechanical and electrical connection with the docking station when docked, wherein the expansion module provides monitoring of one or more additional parameters, the expansion module allowing the patient monitoring system attached to the docking station to monitor the one or more additional parameters.

2. The docking station of claim 1, wherein the first docking arm is attached to the first docking port and the expansion module is attached to the second docking port in a first configuration and wherein the first docking arm is attached to the second docking port and the expansion module is attached to the first docking port in a second configuration.

3. The docking station of claim 1, wherein the portable monitor attaches to a transport dock and the first docking arm is removed so that the transport dock attaches to the first or second docking port.

4. The docking station of claim 1, wherein the portable monitor comprises a monitoring tablet.

5. The docking station of claim 1, wherein the expansion module attaches to a module dock which attaches to the first or second docking port.

6. The docking station of claim 1, wherein the one or more additional parameter comprises at least one of EEG, BP, ECG, temperature and cardiac output.

7. A docking station for a modular patient monitoring system, the docking station comprising:
 a first display oriented in a first direction;
 a docking port configured to receive a monitoring component having a portable display, the docking port forming a mechanical and electrical connection with the monitoring component, the docking port located on a backside of the display;
 a removable docking arm connected to the docking port and extending out from the docking port, the docking arm configured to extend the docking so that the portable display is visible from the first direction without being obscured by the first display, the docking arm further configured to allow the portable display to move from a first orientation to a second orientation relative to the first display; and
 a second docking port configured to receive at least an expansion module, the expansion module forming a mechanical and electrical connection with the docking station when docked, wherein the expansion module provides monitoring of one or more additional parameters, the expansion module allowing the patient monitoring system attached to the docking station to monitor the one or more additional parameters.

8. The docking station of claim 7, wherein the portable display is oriented independently of the first display.

9. The docking station of claim 7, wherein the portable display is oriented by rotating the docking arm along a first axis.

10. The docking station of claim 9, wherein the portable display is oriented by rotating the docking arm along a second axis.

* * * * *